United States Patent [19]
Ferrari et al.

[11] Patent Number: 5,264,366
[45] Date of Patent: Nov. 23, 1993

[54] PROTEASE DEFICIENT BACILLUS

[75] Inventors: Eugenio Ferrari, San Bruno; Dennis J. Henner, Pacifica, both of Calif.; Mark L. Stahl, Arlington, Mass.

[73] Assignee: Genencor, Inc., So. San Francisco, Calif.

[21] Appl. No.: 797,577

[22] Filed: Nov. 25, 1991

Related U.S. Application Data

[63] Continuation of Ser. No. 41,885, Apr. 23, 1987, abandoned, which is a continuation of Ser. No. 614,615, May 29, 1984, abandoned.

[51] Int. Cl.$^5$ .............. C12N 15/00; C12N 15/03; C12N 15/31; C12N 15/75
[52] U.S. Cl. .............. 435/252.31; 435/69.1; 435/222; 435/320.1; 435/172.3; 935/14; 935/27; 935/74
[58] Field of Search .............. 435/222, 320.1, 69.1, 435/172.3, 252.31

[56] References Cited

U.S. PATENT DOCUMENTS

| | | | |
|---|---|---|---|
| 4,266,031 | 5/1981 | Tang et al. | 435/836 |
| 4,284,722 | 8/1981 | Tamuri et al. | 435/202 |
| 4,299,848 | 11/1981 | De Stefanis et al. | 435/202 |
| 4,610,964 | 9/1986 | Lompe | 435/253 |

FOREIGN PATENT DOCUMENTS 0721484  3/1980  U.S.S.R. .............. 435/202

OTHER PUBLICATIONS

Stahl et al J. Bact. vol. 158, pp. 411-418 (1984).
Gutterson, et al Proc Natl Acad Sci USA vol. 80 pp. 4894-4898 (1983).
Scherer et al Proc Natl Acad Sci USA, vol. 76 pp. 4951-4955 (1979).
Wells et al Nucl. Acids Res vol. 11, pp. 7911-7925 (1983).
Itakura, et al Science, vol. 209 pp. 1401-1405 (1980).
Priest, Bacteriological Reviews 41(3) p. 721 (1977).
Lewin, Genes, John Wiley & Sons, NY pp. 42-47 (1983).

Primary Examiner—Robert A. Wax
Assistant Examiner—William W. Moore
Attorney, Agent, or Firm—Margaret A. Horn

[57] ABSTRACT

There are described, normally sporulating mutant Bacillus strain(s) which produce no detectable proteolytic activity during any phase of its growth. The absence of detectable proteolytic activity is due to the deletion of one or more codons specifying the mature subtilisin protease and the mature neutral protease. Also described are methods for producing such normally sporulating, protease deficient Bacillus mutants.

4 Claims, 16 Drawing Sheets

Fig. 2.
Panel A: probe 1 [³²P-AACAA$^C_T$ATGGA$^C_T$GT]
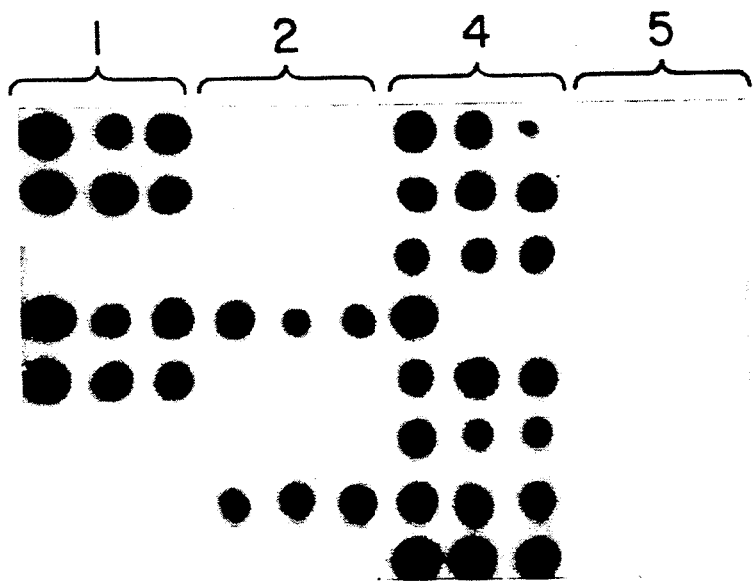
Panel B: probe 2 [³²P-AATAA$^C_T$ATGGA$^C_T$GT]
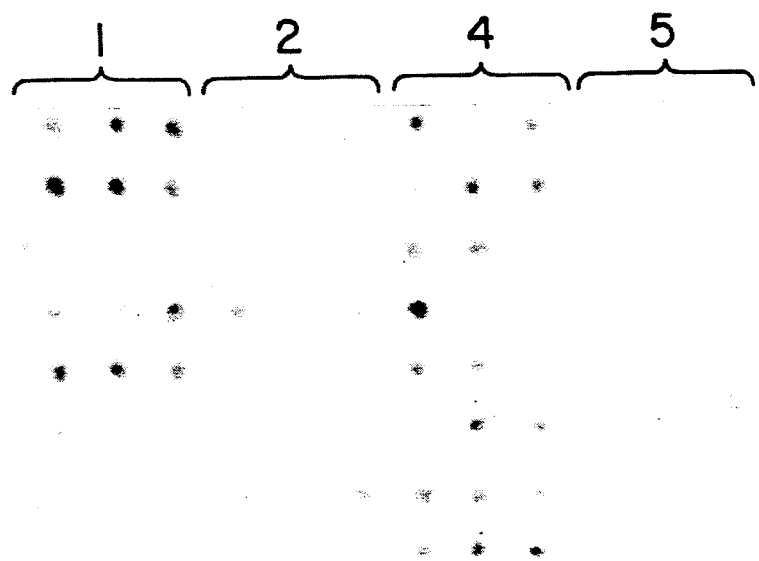

Fig.7

```
   1 GATATACCTAAATAGAGATAAAATCATCTCAAAAAAATGGGTCTACTAAAATATTATTCCATCTATTACAATAAATTCACAGAATAGTCTTTTAAGTAAG

-100
                                       fMet Arg Ser Lys Lys Leu Trp Ile Ser Leu Leu Phe Ala Leu Thr Leu
 101 TCTACTCTGAATTTTTTTAAAAGGAGAGGGTAAAGA GTG AGA AGC AAA AAA TTG TGG ATC AGC TTG TTG TTT GCG TTA ACG TTA
                                         ---------                 ---

-90                                   -80                                   -70
     Ile Phe Thr Met Ala Phe Ser Asn Met Ser Ala Gln Ala Ala Gly Lys Ser Ser Thr Glu Lys Lys Tyr Ile Val
 185 ATC TTT ACG ATG GCG TTC AGC AAC ATG TCT GCG CAG GCT GCC GGA AAA AGC AGT ACA GAA AAG AAA TAC ATT GTC

-60                                   -50
     Gly Phe Lys Gln Thr Met Ser Ala Met Ser Ser Ala Lys Lys Lys Asp Val Ile Ser Glu Lys Gly Gly Lys Val
 260 GGA TTT AAA CAG ACA ATG AGT GCC ATG AGT TCC GCC AAG AAA AAG GAT GTT ATT TCT GAA AAA GGC GGA AAG GTT
                                                                                      -----------
     -40                                   -30                                   -20
     Gln Lys Gln Phe Lys Tyr Val Asn Ala Ala Ala Ala Thr Leu Asp Glu Lys Ala Val Lys Glu Leu Lys Lys Asp
 335 CAA AAG CAA TTT AAG TAT GTT AAC GCG GCC GCA GCA ACA TTG GAT GAA AAA GCT GTA AAA GAA TTG AAA AAA GAT

-10                                   -1  1                                    10
     Pro Ser Val Ala Tyr Val Glu Glu Asp His Ile Ala His Glu Tyr Ala Gln Ser Val Pro Tyr Gly Ile Ser Gln
 410 CCG AGC GTT GCA TAT GTG GAA GAA GAT CAT ATT GCA CAT GAA TAT GCG CAA TCT GTT CCT TAT GGC ATT TCT CAA 20                                  30      32
     Ile Lys Ala Pro Ala Leu His Ser Gln Gly Tyr Thr Gly Ser Asn Val Lys Val Ala Val Ile Asp Ser Gly Ile
 485 ATT AAA GCG CCG GCT CTT CAC TCT CAA GGC TAC ACA GGC TCT AAC GTA AAA GTA GCT GTT ATC GAC AGC GGA ATT 40                                   50                                   60
     Asp Ser Ser His Pro Asp Leu Asn Val Arg Gly Gly Ala Ser Phe Val Pro Ser Glu Thr Asn Pro Tyr Gln Asp
 560 GAC TCT TCT CAT CCT GAC TTA AAC GTC AGA GGC GGA GCA AGC TTC GTA CCT TCT GAA ACA AAC CCA TAC CAG GAC 64                      70                                   80
     Gly Ser Ser His Gly Thr His Val Ala Gly Thr Ile Ala Ala Leu Asn Asn Ser Ile Gly Val Leu Gly Val Ser
 635 GGC AGT TCT CAC GGT ACG CAT GTA GCC GGT ACG ATT GCC GCT CTT AAT AAC TCA ATC GGT GTT CTG GGC GTT AGC 90                                  100                                  110
     Pro Ser Ala Ser Leu Tyr Ala Val Lys Val Leu Asp Ser Thr Gly Ser Gly Gln Tyr Ser Trp Ile Ile Asn Gly
 710 CCA AGC GCA TCA TTA TAT GCA GTA AAA GTG CTT GAT TCA ACA GGA AGC GGC CAA TAT AGC TGG ATT ATT AAC GGC 120                                 130
     Ile Glu Trp Ala Ile Ser Asn Asn Met Asp Val Ile Asn Met Ser Leu Gly Gly Pro Thr Gly Ser Thr Ala Leu
 785 ATT GAG TGG GCC ATT TCC AAC AAT ATG GAT GTT ATC AAC ATG AGC CTT GGC GGA CCT ACT GGT TCT ACA GCG CTG 140                                  150                                 160
     Lys Thr Val Val Asp Lys Ala Val Ser Ser Gly Ile Val Val Ala Ala Ala Ala Gly Asn Glu Gly Ser Ser Gly
 860 AAA ACA GTC GTT GAC AAA GCC GTT TCC AGC GGT ATC GTC GTT GCT GCC GCA GCC GGA AAC GAA GGT TCA TCC GGA 170                                  180
     Ser Thr Ser Thr Val Gly Tyr Pro Ala Lys Tyr Pro Ser Thr Ile Ala Val Gly Ala Val Asn Ser Ser Asn Gln
 935 AGC ACA AGC ACA GTC GGC TAC CCT GCA AAA TAT CCT TCT ACT ATT GCA GTA GGT GCG GTA AAC AGC AGC AAC CAA 190                                  200                                  210
     Arg Ala Ser Phe Ser Ser Ala Gly Ser Glu Leu Asp Val Met Ala Pro Gly Val Ser Ile Gln Ser Thr Leu Pro
1010 AGA GCT TCA TTC TCC AGC GCA GGT TCT GAG CTT GAT GTG ATG GCT CCT GGC GTG TCC ATC CAA AGC ACA CTT CCT 220 221                             230
     Gly Gly Thr Tyr Gly Ala Tyr Asn Gly Thr Ser Met Ala Thr Pro His Val Ala Gly Ala Ala Ala Leu Ile Leu
1085 GGA GGC ACT TAC GGC GCT TAT AAC GGA ACG TCC ATG GCG ACT CCT CAC GTT GCC GGA GCA GCA GCG TTA ATT CTT 240                                     250                                 260
     Ser Lys His Pro Thr Trp Thr Asn Ala Gln Val Arg Asp Arg Leu Glu Ser Thr Ala Thr Tyr Leu Gly Asn Ser
1160 TCT AAG CAC CCG ACT TGG ACA AAC GCG CAA GTC CGT GAT CGT TTA GAA AGC ACT GCA ACA TAT CTT GGA AAC TCT

270
     Phe Tyr Tyr Gly Lys Gly Leu Ile Asn Val Gln Ala Ala Ala Gln OC
1235 TTC TAC TAT GGA AAA GGG TTA ATC AAC GTA CAA GCA GCT GCA CAA TAA TAGTAAAAAGAAGCAGGTTCCTCCATACCTGCTTC
                                                            ---             ----------------          ---------

1318 TTTTTATTTGTCAGCATCCTGATGTTCCGGCGCATTCTCTTCTTTCTCCGCATGTTGAATCCGTTCCATGATCGACGGATGGCTGCCTCTGAAAATCTTC
     ------

1418 ACAAGCACCGGAGGATCAACCTGCTCAGCCCCGTCACGGCCAAATCCTGAAACGTTTTAACACTGGCTTCTCTGTTCTCTGTC
```

Fig.10.

```
                    CACATGACAC TTGACTCATC TTGATATTAT TCACAAAAA CAAACACAGG ACAATACTAT CAATTTGTC TAGTTATGTT AGTTTTGTT GAGTATTCCA GAATGCTAGT TTAATATAAC AATATAAAGT TTTCAGTATT
TTCAAAAAGG GGGATTTATT
                             1                                   10                          20                                  30
                             met gly leu gly lys leu val arg val ala ser phe met ser leu pro gly val gln ile ala ala glu gly his gln leu lys
                             GTG GGT TTA GGT AAG AAA TTG TCT GTT CGT GCT GCT TCG TTT ATG AGT TTA TCA ATC AGC CTG CCA GGT GTT CAG GCT GAA GGT CAT CAG CTT AAA
     40                                   50                                   60                                   70
glu asn gln thr asn phe lys ser lys pro ile ala ser ala asp asn ala ala lys val gln leu lys asn asn ile phe lys gly lys asp pro
GAG AAT CAA ACA AAT TTC CTC AAA ACG CCG ATT GCG CAA TCA GAA CTC TCT GCA CCA AAT GAC AAG GCT GTT TTG AAA AAG AAC AGC ATT TTT AAA GGT AAG GAT CCT
                 80                                   90                                  100                                  110
ser lys ser val lys leu val leu glu ser thr asp ala arg tyr lys his phe arg val ala pro val val asn gly val pro ile lys asp val ile val his val asp
TCC AAG AGC GTG AAG CTT GTT GAA AGC ACG GAT GCT CGT TAC AAG CAC TTT CGA TAT GCG CCT GTT GCA CCA GTT AAC GGA GTA CCA ATT AAA GAT GTC CAC GTC GAT
                         120                                  130                                  140                                  150
lys ser asp asn val tyr ala val asn gly glu leu his asn gln ser ala thr lys asn gln val ser val ser glu lys ala leu ala leu phe lys ala ile gly
AAA TCC GAT AAT GTC TAT GCG GTC AAT GGT GAA TTA CAC AAT CAA TCT GCT GCA AAA ACA GAT AAC AGC CAA AAA GTC TCT GAA AAA GCG CTG GCA CTC GCT TTC AAA GCT ATC GGC
                                 160                                  170                                  180                                  190
lys ser pro asp ala val ser asn gly val ser asn gly ala ile glu leu lys ala ile leu ala ile glu thr lys asp tyr arg leu val thr val thr ile arg tyr val
AAA TCA CCA GAC GCT GTT TCT AAC GGA GTA AGT AAC GGT GCA ATA GAA TTA AAA GCG ATA CTT GCT CTT GCT TAC GAC GTG ACG ATT CGC TAT GTC
                                         200                                  210                                  220   Mature                230
glu pro gly glu pro asn trp gly val leu val glu his ala ala ile glu leu lys ala thr asp tyr gly tyr thr thr lys val ala lys ala
GAG CCT GAA CCT GAA AAC TGG GGA GTC TTA GTT GAA CAT GCC GCC ACT GGA ATC GCC ACT AAA GCA ACG GAT TAT GGT TAC GAC ACG ACA AAG GCA
                                                 240                                  250                                  260                                  270
thr val pro leu asn ile ser tyr val phe thr ser ser val tyr val leu val ser gly lys pro thr gly thr gly gln ile ile thr tyr asn leu gln asn arg gln asn gln ser arg leu pro gly
ACT GTT CCT TTG AAC ATC TCT TAT GTT TTC ACA TCT TCA GTT TAT GTT CTA AGA GAT CTT TCA AAA CCA ACA GGC ACC CAA ATC ATC ACA TAT AAT TTG CAA AAC AGA CAA AAC CAG TCT CGG CTT CCG GGC
                                                         280                                  290                                  300                                  310
thr leu val ser thr thr thr lys ile val ser gln gln arg ala asp ala his tyr lys val tyr gly lys leu gly asn ala trp thr ala asn leu tyr ala leu arg phe asn ser
ACG CTT GTC TCA AGC ACA ACA AAA ATC GTT TCT CAA CAG CGG GCA GAC GCA CAT TAC AAG GTC TAT GGT AAA CTC GGT AAT GCC TGG ACT GCA AAT CTG TAT GCC CTT CGA TTC AAC AGT
                                                                 320                                  330                                  340                                  350
tyr asp asn lys gly ser lys ile val his glu met thr ala his val gln thr gln glu asn ala ala trp thr gly val ala glu leu asn gln ser pro phe ser pro val phe
TAT GAT AAC AAA GGC AGT AAA ATC GTT TCT CAC GTT CAA ACA CAT GGT ATG ACG GCA CAT GTG CAA ACT CAA GAA AAT GCA GCA TGG ACA GGA GTT GCT GAA CTG AAT CAG TCT CCG TTC TCT CCG GTA TTC
                                                                         360                                  370                                  380                                  390
leu ser gly val leu asp val leu asp val thr his ala his thr ala ile his gly met thr gln thr ala asn ala ile glu leu ala ser asn pro thr lys tyr arg asn thr leu asn gly val ala glu tyr val phe
CTT TCC GGC TCA TTA GAT GTG ACA GCG CAT GAA ATG ACA CAT GCC GTC ACG GCA ATT CAT GGA ATG ACG CAA ACG GCC AAC GCC ATT GAA CTG GCA TCG AAC CCT ACA AAG TAC CGC AAT ACG TTG AAC GGT GTA GCG GAG TAC GTA TTC
                                                                                 400                                  410                                  420                                  430
gly tyr phe asn asp thr glu thr asp ile gly asp trp gly tyr gly val his thr asn val ser gln pro ala leu arg ser asn thr lys tyr ala ala ala leu ser gln pro asn tyr ala asn tyr
GGG TAT TTT AAC GAT ACA GAA GAC TGG GGC GAT ATC GGT GAT GGC GAT TAT GGC GGT GTA CAC ACA AAT GTT TCA CAG CCT GCT CTT CGC AGC AAC ACG AAA TAC GCT GCG GCT TTA TCG CAA CCT AAC TAC GCC AAT TAC
                                                                                         440                                  450                                  460                                  470
arg asn leu asp thr asp ser glu gln asp gly val gly tyr gly val his ser asn val ser gln pro ala leu arg gly lys pro asn tyr asp lys lys ser gln ala ile ser gln pro gln ile
CGA AAC CTT GAT ACA GAC AGC GAA CAA GAT GGA GTA GGC TAT GGC GGT GTA CAC AGC AAC GTA AGC CAG CCT GCT CTA CGG GGC AAA CCG AAT TAC GAC AAA AAA TCA CAG GCA ATC TCA CAG CCA CAA ATC
                                                                                                 480                                  490                                  500                                  510
tyr tyr arg gly ala leu thr thr leu pro leu thr tyr ser ser pro thr phe pro lys ala ser ala ala leu gln gln ala ala arg asp leu tyr gly ser thr lys asp leu ser ala ala ile lys val gly ala
TAT TAC CGT GGT GCG TTA ACA ACG TTA CCT CTC ACG TCT TCC ACG ACT CAG CCC ATT CAG GAC TCT GCC AAG GCG GCG CTC AAG CAA GCC GCA CGT GAT CTG TAC GGC TCA ACT AAA GAT CTA AGC GCT GCT ATT AAG GTC GGG GCA
                                                                                                         520 521
ala trp asn ala val gly leu OC
GCC TGG AAT GCT GTT GGA TTG TAA TATTAGAAA AGCCTGAGT CCCTGAGCT TTATTGTTA CATATCTTGA TTTTCTCTC AGCTGAAACG ACAAAAGAT GCTGCCATGA GACAAGAAAC CGCTCTCTGT TTGCATAAAG AAGGATGCAG GCGGAAAGTGC CCGTAAATGC GCATTTATA AAAGCTAATG ATGCAGCTCCA CATAATTGAT AGACGAATTC
```

Fig.12.

```
                                                    codon:                          220   222                              230
Wild type amino acid sequence:                               Ala Tyr Asn Gly Thr Ser Met Ala Ser Pro His Val Ala Gly Ala Ala 1. Wild type DNA sequence:              5'-GCG TAC AAC GGT ACG TCA ATG GCA TCT CCG CAC GTT GCC GGA GCG GCT-3'
                                        3'-CGC ATG TTG CCA TGC AGT TAC CGT AGA GGC GTG CAA CGG CCT CGC CGA-5'

*                                *   *
2. Δp222 DNA sequence:                  5'-GCG TAC AAC GGT ACC TCA----------CG CAC GCT GCA GGA GCG GCT-3'
                                        3'-CGC ATG TTG CCA TGG AGT          GC GTG CGA CGT CCT CGC CGA-5'
                                                             KpnI                     PstI

*
3. Δp222 cut with KpnI and PstI:        5'-GCG TAC AAC GGT AC                               pGGA GCG GCT-3'
                                        3'-CGC ATG TTG CCA TGG Cp                          A CGT CGC CGA-5'

***                          *
4. cut Δp222 ligated with oligo-        5'-GCG TAC AAC GGT ACG TCA NNN GCA TCT CCG CAC GTT GCA GGA GCG GCT-3'
   nucleotide pools:                    3'-CGC ATG TTG CCA TGC AGT NNN CGT AGA GGC GTG CAA CGT CCT CGC CGA-5'
```

Fig. 13.

Wild type amino acid sequence:  thr ser gly ser ser ser thr var gly tyr pro gly

1. Wild type DNA sequence:
```
5' ACT TCC GGC AGC TCA AGC ACA GTC GGC TAC CCT GGT 3'
3' TCA AGG CCG TCG AGT TCG TGT CAG CCG ATG GGA CCA 5'
```

*                              *
2. Δp166
```
5' ACT TCC GGG AGC TCA A - - - - - - - -      C CCG GGT 3'
3' TGA AGG CCC TCG AGT T                      G GGC CCA 5'
```

*                                  *
3. Δp166 cut with
   SacI and XmaIII
```
5' ACT TCC GGG AGC T                          pCCG GGT 3'
3' TGA AGG CCCp                                    CA 5'
```

*                       *                         *
4. Cut Δp166 ligated with
   oligonucleotide pools
```
5' ACT TCC GGG AGC TCA AGC ACG GTC NNN TAT CCG GGT 3'
3' TGA AGG CCC TCG AGT TCG TGT CAG NNN ATA GGC CCA 5'
```

Mutagenesis primer 37mer
```
5' AA GGC ACT TCC GGG AGC TCA ACC CGG GTA AA  TAC CCT 3'
```

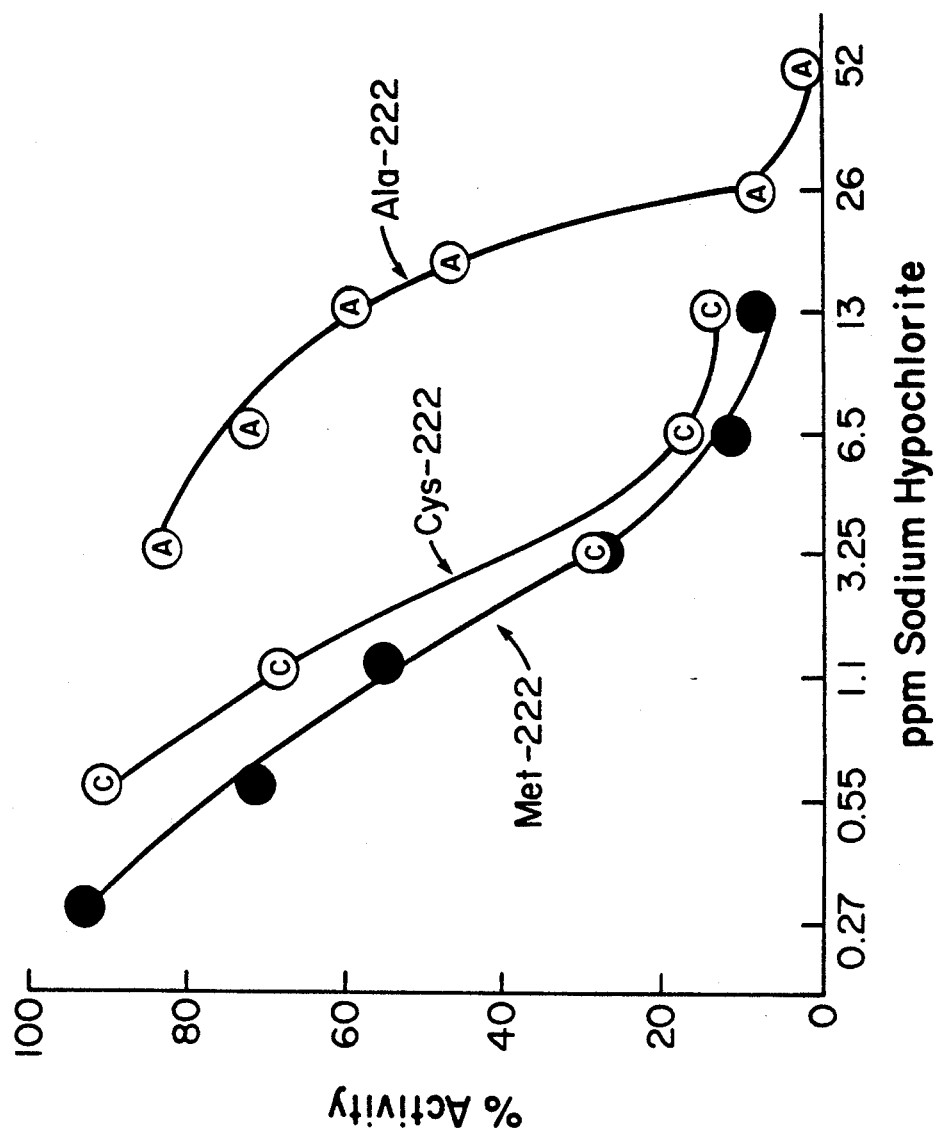
Fig. 14. OXIDATIVE STABILITY OF THE CYS-222 AND ALA-222 MUTANTS

Fig. 16.

G-169 Saturation Mutagenesis

```
                    codon:           162                        169                      173
Wild type amino acid sequence:   ser ser thr val gly tyr pro gly lys tyr pro ser 1. Wild type DNA sequence:       5'-TCA AGC ACA GTG GGC TAC CCT GGT AAA TAC CCT TCT-3'
                                 3'-AGT TCG TGT CAC CCG ATG GGA CCA TTT ATG GGA AGA-5'
                                                              *             *
2. Δp169 DNA sequence:           5'-TCA AGC ACA GTG GGG TAC CCT-----GA TAT CCT TCT-3'
                                 3'-AGT TCG TGT CAC CCC ATG GGA-----CT ATA GGA AGA-5'
                                                      KpnI            EcoRV 3. Δp169 cut with KpnI and EcoRV: 5'-TAC AGC ACA GTC GGG TAC              pAT CCT TCT-3'
                                  3'-AGT TCG TGT CAC CCp                   TA GGA AGA-5'
                                                                        *
4. cut Δp169 ligated with oligo-  5'-TAC AGC ACA GTG GGG TAC CCT NNN AAA TAT CCT TGT-5'
   nucleotide pools:              3'-AGT TCG TGT CAC CCC ATG GGA NNN TTT ATA GGA AGA-3'

Mutagenesis primer for Δp169     5'-AAG CAC AGT GGG GTA CCC TGA TAT CCT TCT GTC A-3'
```

PROTEASE DEFICIENT BACILLUS

CROSS-REFERENCE TO RELATED APPLICATIONS

This is a continuation of application Ser. No. 041,885 filed Apr. 23, 1987, now abandoned, which is a continuation of application Ser. No. 614,615 filed May 29, 1984, now abandoned. Cross-reference is made to application Ser. No. 507,419 filed Jun. 24, 1983, and its continuation Ser. No. 614,616 filed May 29, 1984, abandoned in favor of Ser. No. 866,389 filed May 22, 1986. Cross reference is made to application Ser. No. 614,612 filed May 29, 1984, application Ser. No. 614,617 field May 29, 1984, and application Ser. No. 614,491 filed May 29, 1984, abandoned in favor of Ser. No. 924,162 filed Oct. 29, 1986.

BACKGROUND

This invention relates to the production and manipulation of proteins using recombinant techniques in suitable hosts. More specifically, the invention relates to the production of procaryotic proteases such as subtilisin and neutral protease using recombinant microbial host cells, to the synthesis of heterologous proteins by microbial hosts, and to the directed mutagenesis of enzymes in order to modify the characteristics thereof.

Various bacterial are known to secrete proteases at some stage in their life cycles. Bacillus species produce two major extracellular proteases, a neutral protease (a metalloprotease inhibited by EDTA) and an alkaline protease (or subtilisin, a serine endoprotease). Both generally are produced in greatest quantity after the exponential growth phase, when the culture enters stationary phase and begins the process of sporulation. The physiological role of these two proteases is not clear. They have been postulated to play a role in sporulation (J. Hoch, 1976, "Adv. Genet." 18:69-98; P. Piggot et al., 1976, "Bact. Rev." 40:908-962; and F. Priest., 1977, "Bact. Rev." 41:711-753), to be involved in the regulation of cell wall turnover (L. Jolliffe et al., 1980, "J. Bact." 141:1199-1208), and to be scavenger enzymes (Priest, Id.). The regulation of expression of the protease genes is complex. They appear to be coordinately regulated in concert with sporulation, since mutants blocked in the early stages of sporulation exhibit reduced-levels of both the alkaline and neutral protease. Additionally, a number of pleiotropic mutations exist which affect the level of expression of proteases and other secreted gene products, such as amylase and levansucrase (Priest, Id.).

Subtilisin has found considerable utility in industrial and commercial applications (see U.S. Pat. No. 3,623,957 and J. Millet, 1970, "J. Appl. Bact." 33:207). For example, subtilisins and other proteases are commonly used in detergents to enable removal of protein-based stains. They also are used in food processing to acconinodate the proteinaceous substances present in the food preparations to their desired impact on the composition.

Classical mutagenesis of bacteria with agents such as radiation or chemicals has produced a plethora of mutant strains exhibiting different properties with respect to the growth phase at which protease excretion occurs as well as the timing and activity levels of excreted protease. These strains, however, do not approach the ultimate potential of the organisms because the mutagenic process is essentially random, with tedious selection and screening required to identify organisms which even approach the desired characteristics. Further, these mutants are capable of reversion to the parent or wild-type strain. In such event the desirable property is lost. The probability of reversion is unknown when dealing with random mutagenesis since the type and site of mutation is unknown or poorly characterized. This introduces considerable uncertainty into the industrial process which is based on the enzyme-synthesizing bacterium. Finally, classical mutagenesis frequently couples a desirable phenotype, eg., low protease levels, with an undesirable character such as excessive premature cell lysis.

Special problems exist with respect to the proteases which are excreted by Bacillus. For one thing, since at least two such proteases exist, screening for the loss of only one is difficult. Additionally, the large number of pleiotropic mutations affecting both sporulation and protease production make the isolation of true protease mutations difficult.

Temperature sensitive mutants of the neutral protease gene have been obtained by conventional mutagenic techniques, and were used to map the position of the regulatory and structural gene in the Bacillus subtilis chromosome (H. Uehara et al., 1979, "J. Bact." 139:583-590). Additionally, a presumed nonsense mutation of the alkaline protease gene has been reported (C. Roitsch et al., 1983, "J. Bact." 155:145-152).

Bacillus temperature sensitive mutants have been isolated that produce inactive serine protease or greatly reduced levels of serine protease. These mutants, however, are asporogenous and show a reversion frequency to the wild-type of about from $10^{-7}$ to $10^{-8}$ (F. Priest, Id. p. 719). These mutants are unsatisfactory for the recombinant production of heterologous proteins because asporogenous mutants tend to lyse during earlier stages of their growth cycle in minimal medium than do sporogenic mutants—thereby prematurely releasing cellular contents (including intracellular proteases) into the culture supernatant. The possibility of reversion also is undesirable since wild-type revertants will contaminate the culture supernatant with excreted proteases.

Bacillus sp. have been proposed for the expression of heterologous proteins, but the presence of excreted proteases and the potential resulting hydrolysis of the desired product has retarded the commercial acceptance of Bacillus as a host for the expression of heterologous proteins. Bacillus megaterium mutants have been disclosed that are capable of sporulation and which do not express a sporulation-associated protease during growth phases. However, the assay employed did not exclude the presence of other proteases, and the protease in question is expressed during the sporulation phase (C. Loshon et al., 1982, "J. Bact." 150:303-311). This, of course, is the point at which heterologous protein would have accumulated in the culture and be vulnerable. It is an objective herein to construct a Bacillus strain that is substantially free of extracellular neutral and alkaline protease during all phases of its growth cycle and which exhibits substantially normal sporulation characteristics. A need exists for non-revertible, otherwise normal protease deficient organisms that can then be transformed with high copy number plasmids for the expression of heterologous or homologous proteins.

Enzymes having characteristics which vary from available stock are required. In particular, enzymes having enhanced oxidation stability will be useful in extending the shelf life and bleach compatibility of proteases used in laundry products. Similarly, reduced oxidation stability would be useful in industrial processes that require the rapid and efficient quenching of enzymatic activity.

Modifying the ph-activity profiles of an enzyme would be useful in making the enzymes more efficient in a wide variety of processes, e.g. broadening the ph-activity profile of a protease would produce an enzyme more suitable for both alkaline and neutral laundry products. Narrowing the profile, particularly when combined with tailored substrate specificity, would make enzymes in a mixture more compatible, as will be further described herein.

Mutations of procaryotic carbonyl hydrolases (principally proteases but including lipases) will facilitate preparation of a variety of different hydrolases, particularly those having other modified properties such as Km, Kcat, Km/Kcat ratio and substrate specificity. These enzymes can then be tailored for the particular substrate which is anticipated to be present, for example in the preparation of peptides or for hydrolytic processes such as laundry uses.

Chemical modification of enzymes is known. For example, see I. Svendsen, 1976, "Carlsberg Res. Commun." 41 (5): 237-291. These methods, however, suffer from the disadvantages of being dependent upon the presence of convenient amino acid residues, are frequently nonspecific in that they modify all accessible residues with common side chains, and are not capable of reaching inaccessible amino acid residues without further processing, e.g. denaturation, that is generally not completely reversible in reinstituting activity. To the extent that such methods have the objective of replacing one amino acid residue side chain for another side chain or equivalent functionality, then mutagenesis promises to supplant such methods.

Predetermined, site-directed mutagenesis of TRNA synthetase in which a cys residue is converted to serine has been reported (G. Winter et al., 1982, "Nature" 299:756-758-1 A. Wilkinson et al., 1984, "Nature" 307:187-188). This method is not practical for large scale mutagenesis. It is an object herein to provide a convenient and rapid method for mutating DNA by saturation mutagenesis.

SUMMARY

A method for producing procaryotic carbonyl hydrolase such as subtilisin and neutral protease in recombinant host cells is described in which expression vectors containing sequences which encode desired subtilisin or neutral protease, including the pro, pre, or prepro forms of these enzymes, are used to transform hosts, the host cultured and desired enzymes recovered. The coding sequence may correspond exactly to one found in nature, or may contain modifications which confer desirable properties on the protein that is produced, as is further described below.

The novel strains then are transformed with at least one DNA moiety encoding a polypeptide not otherwise expressed in the host strain, the transformed strains cultured and the polypeptide recovered from the culture. Ordinarily, the DNA moiety is a directed mutant of a host Bacillus gene, although it may be DNA encoding a eucaryotic (yeast or mammalian) protein. The novel strains also serve as hosts for protein expressed from a bacterial gene derived from sources other than the host genome, or for vectors expressing these heterologous genes, or homologous genes from the host genome. In the latter event enzymes such as amylase are obtained free of neutral protease or subtilisin. In addition, it is now possible to obtain neutral protease in culture which is free of enzymatically active subtilisin, and vice-versa.

One may, by splicing the cloned genes for procaryotic carbonyl hydrolase into a high copy number plasmid, synthesize the enzymes in enhanced yield compared to the parental organisms. Also disclosed are modified forms of such hydrolases, including the pro and prepro zymogen forms of the enzymes, the pre forms, and directed mutations thereof.

A convenient method is provided for saturation mutagenesis, thereby enabling the rapid and efficient generation of a plurality of mutations at any one site within the coding region of a protein, comprising;

(a) obtaining a DNA moiety encoding at least a portion of said precursor protein;
(b) identifying a region within the moiety;
(c) substituting nucleotides for those already existing within the region in order to create at least one restriction enzyme site unique to the moiety, whereby unique restriction sites 5' and 3' to the identified region are made available such that neither alters the amino acids coded for by the region as expressed;
(d) synthesizing a plurality of oligonucleotides, the 5' and 3' ends of which each contain sequences capable of annealing to the restriction enzyme sites introduced in step (c) and which, when ligated to the moiety, are expressed as substitutions, deletions and/or insertions of at least one amino acid in or into said precursor protein;
(e) digesting the moiety of step (c) with restriction enzymes capable of cleaving the unique sites; and
(f) ligating each of the oligonucleotides of step (d) into the digested moiety of step (e) whereby a plurality of mutant DNA moieties are obtained.

By the foregoing method or others known in the art, a mutation is introduced into isolated DNA encoding a procaryotic carbonyl hydrolase which, upon expression of the DNA, results in the substitution, deletion or insertion of at least one amino acid at a predetermined site in the hydrolase. This method is useful in creating mutants of wild type proteins (where the "Precursor" protein is the wild type) or reverting mutants to the wild type (where the "precursor" is the mutant.

Mutant enzymes are recovered which exhibit oxidative stability and/or ph-activity profiles which differ from the precursor enzymes. Procaryotic carbonyl hydrolases having varied Km, Kcat, Kcat/Km ratio and substrate specificity also are provided herein.

The mutant enzymes obtained by the methods herein are combined in known fashion with surfactants or detergents to produce novel compositions useful in the laundry or other cleaning arts.

BRIEF DESCRIPTION OF THE DRAWINGS

In FIG. 1A, the entire functional sequence for *B. amyloliquefaciens*, including the promoter and ribosome binding site, are present on a 1.5 kb fragment of the *B. amyloliquefaciens* genome.

FIG. 1B shows the nucleotide sequence of the coding strand, correlated with the amino acid sequence of the protein. Promoter (p) ribosome binding site (rbs) and termination (tem) regions of the DNA sequence are also shown.

FIG. 2 shows the results of replica nitrocellulose filters of purified positive clones probed with Pool 1 (Panel A) and Pool 2 (Panel B) respectively.

FIG. 7 is the sequence of a functional B. subtilis subtilisin gene.

FIG. 10 is the nucleotide sequence for a B. subtilis neutral protease gene.

FIGS. 12, 13 and 16 disclose embodiments of the mutagenesis technique provided herein.

FIG. 14 shows the enhanced oxidation stability of a subtilisin mutant.

DETAILED DESCRIPTION

Figure 1:
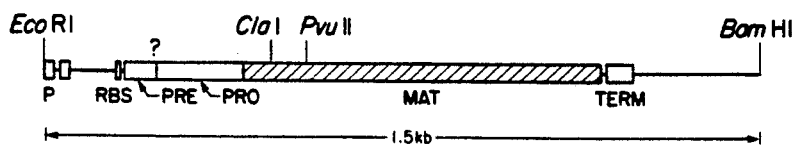
FIG. 1 shows the sequence of a functional *B. amyloliquefaciens* subtilisin gene.

Procaryotic carbonyl hydrolases are enzymes which hydrolyze compounds containing

bonds in which X is oxygen or nitrogen. They principally include hydrolases, e.g. lipases and peptide hydrolases, e.g. subtilisins or metalloproteases. Peptide hydrolases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

Subtilisins are serine proteinases which generally act to cleave internal peptide bonds of proteins or peptides. Metalloproteases are exo- or endoproteases which require a metal ion cofactor for activity.

A number of naturally occurring mutants of subtilisin or neutral protease exist, and all may be employed with equal effect herein as sources for starting genetic material.

These enzymes and their genes may be obtained from many procaryotic organisms. Suitable examples include gram negative organisms such as E.coli or pseudomonas and gram positive bacteria such as micrococcus or bacillus.

The genes encoding the carbonyl hydrolase may be obtained in accord with the general method herein. As will be seen from the examples, this comprises synthesizing labelled probes having putative sequences encoding regions of the hydrolase of interest, preparing genomic libraries from organisims expressing the hydrolase, and screening the libraries for the gene of interest by hybridization to the probes. Positively hybridizing clones are then mapped and sequenced. The cloned genes are ligated into an expression vector (which also may be the cloning vector) with requisite regions for replication in the host, the plasmid transfected into a host for enzyme synthesis and the recombinant host cells cultured under conditions favoring enzyme synthesis, usually selection pressure such as is supplied by the presence of an antibiotic, the resistance to which is encoded by the vector. Culture under these conditions results in enzyme yields multifold greater than the wild type enzyme synthesis of the parent organism, even if it is the parent organism that is transformed.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form, of vector at present. However, the invention is intended to include such other forms of expression vectors which serve equivalent functions and which are, or become, known in the art.

"Recombinant host cells" refers to cells which have been transformed or transfected with vectors constructed using recombinant DNA techniques. As relevant to the present invention, recombinant host cells are those which produce procaryotic carbonyl hydrolases in its various forms by virtue of having been transformed with expression vectors encoding these proteins. The recombinant host cells may or may not have produced a form of carbonyl hydrolase prior to transformation.

"Operably linked" when describing the relationship between two DNA regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

"Prohydrolase" refers to a hydrolase which contains additional N-terminal amino acid residues which render the enzyme inactive but, when removed, yield an enzyme. Many proteolytic enzymes are found in nature as translational proenzyme products and, in the absence of post-translational products, are expressed in this fashion.

"Presequence" refers to a signal sequence of amino acids bound to the N-terminal portion of the hydrolase which may participate in the secretion of the hydrolase. Presequences also may be modified in the same fashion as is described here, including the introduction of predetermined mutations. When bound to a hydrolase, the subject protein becomes a "prehydrolase". Accordingly, relevant prehydrolase for the purposes herein are presubtilisin and preprosubtilisin. Prehydrolases are produced by deleting the "pro" sequence (or at least that portion of the pro sequence that maintains the enzyme in its inactive state) from a prepro coding region, and then expressing the prehydrolase. In this way the organism excretes the active rather than proenzyme.

The cloned carbonyl hydrolase is used to transform a host cell in order to express the hydrolase. This will be of interest where the hydrolase has commercial use in its unmodified form, as for example subtilisin in laundry products as noted above. In the preferred embodiment the hydrolase gene is ligated into a high copy number plasmid. This plasmid replicates in hosts in the sense that it contains the well-known elements necessary for plasmid replication: a promoter operably linked to the gene in question (which may be supplied as the gene's own homologous promotor if it is recognized, i.e., transcribed, by the host), a transcription termination and polyadenylation region (necessary for stability of the mRNA transcribed by the host from the hydrolase gene) which is exogenous or is supplied by the endogenous terminator region of the hydrolase gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosonal limitations. However, it is within the scope herein to integrate multiple copies of the hydrolase gene into host genome. This is facilitated by bacterial strains which are particularly susceptible to homologous recombination. The resulting host cells are termed recombinant host cells.

Once the carbonyl hydrolase gene has been cloned, a number of modifications are undertaken to enhance the use of the gene beyond synthesis of the wild type or precursor enzyme. A precursor enzyme is the enzyme prior to its modification as described in this application. Usually the precursor is the enzyme as expressed by the organism which donated the DNA modified in accord herewith. The term "precursor" is to be understood as not implying that the product enzyme was the result of manipulation of the precursor enzyme per se.

In the first of these modifications, the gene may be deleted from a recombination positive (rec+) organism containing a homologous gene. This is accomplished by recombination of an in vitro deletion mutation of the cloned gene with the genome of the organism. Many strains of organisms such as E.coli and Bacillus are known to be capable of recombination. All that is needed is for regions of the residual DNA from the deletion mutant to recombine with homologous regions of the candidate host. The deletion may be within the coding region (leaving enzymatically inactive polypeptides) or include the entire coding region as long as homologous flanking regions (such as promoters or termination regions) exist in the host. Acceptability of the host for recombination deletion mutants is simply determined by screening for the deletion of the transformed phenotype. This is most readily accomplished in the case of carbonyl hydrolase by assaying host cultures for loss of the ability to cleave a chromogenic substrate otherwise hydrolyzed by the hydrolase.

Transformed hosts contained the protease deletion mutants are useful for synthesis of products which are incompatible with proteolytic enzymes. These hosts by definition are incapable of excreting the deleted proteases described herein, yet are substantially normally sporulating. Also the other growth characteristics of the transformants are substantially like the parental organism. Such organisms are useful in that it is expected they will exhibit comparatively less inactivation of heterologous proteins than the parents, and these hosts do have growth characteristics superior to known protease-deficient organisms. However, the deletion of neutral protease and subtilisin as described in this application does not remove all of the proteolytic activity of Bacillus. It is believed that intracellular proteases which are not ordinarily excreted extracellularly "leak" or diffuse from the cells during late phases of the culture. These intracellular proteases may or may not be subtilisin or neutral protease as those enzymes are defined herein. Accordingly, the novel Bacillus strains herein are incapable of excreting the subtilisin and/or neutral protease enzymes which ordinarily are excreted extracellularly in the parent strains. "Incapable" means not revertible to the wild type. Reversion is a finite probability that exists with the heretofore known protease-deficient, naturally occurring strains since there is no assurance that the phenotype of such strains is not a function of a readily revertible mutation, e.g. a point mutation. This to be contrasted with the extremely large deletions provided herein.

The deletion mutant-transformed host cells herein are free of genes encoding enzymatically active neutral protease or subtilisin, which genes are defined as those being substantially homologous with the genes set forth in FIGS. 1, 7 or 10. "Homologous" genes contain coding regions capable of hybridizing under high stringency conditions with the genes shown in FIGS. 1, 7 or 10.

The microbial strains containing carbonyl hydrolase deletion mutants are useful in two principal processes. In one embodiment they are advantageous in the fermentative production of products ordinarily expressed by a host that are desirably uncontaminated with the protein encoded by the deletion gene. An example is fermentative synthesis of amylase, where contaminant proteases interfere in many industrial uses for amylase. The novel strains herein relieve the art from part of the burden of purifying such products free of contaminating carbonyl hydrolases.

In a-second principal embodiment, subtilisin and neutral protease deletion-mutant strains are useful in the synthesis of protein which is not otherwise encoded by the strain. These proteins will fall within one of two classes. The first class consists of proteins encoded by genes exhibiting no substantial pretransformation homology with those of the host. These may be proteins from other procaryotes but ordinarily are eucaryotic proteins from yeast or higher eucaryotic organisms, particularly mammals. The novel strains herein serve as useful hosts for expressible vectors containing genes encoding such proteins because the probability for proteolytic degradation of the expressed, non-homologous proteins is reduced.

The second group consists of mutant host genes exhibiting substantial pretransformation homology with those of the host. These include mutations of procaryotic carbonyl hydrolases such as subtilisin and neutral protease, as well as microbial (rennin, for example rennin from the genus Mucor). These mutants are selected in order to improve the characteristics of the precursor enzyme for industrial uses.

A novel method is provided to facilitate the construction and identification of such mutants. First, the gene encoding the hydrolase is obtained and sequenced in whole or in part. Then the sequence is scanned for a point at which it is desired to make a mutation (deletion, insertion or substitution) of one or more amino acids in the expressed enzyme. The sequences flanking this point are evaluated for the presence of restriction sites for replacing a short segment of the gene with an oligonucleotide pool which when expressed will encode various mutants. Since unique restriction sites are generally not present at locations within a convenient distance from the selected point (from 10 to 15 nucleotides), such sites are generated by substituting nucleotides in the gene in such a fashion that neither the reading frame nor the amino acids encoded are changed in the final construction. The task of locating suitable flanking regions and evaluating the needed changes to arrive at two unique restriction site sequences is made routine by the redundancy of the genetic code, a restriction enzyme map of the gene and the large number of different restriction enzymes. Note that if a fortuitous flanking unique restriction site is available, the above method need be used only in connection with the flanking region which does not contain a site.

Mutation of the gene in order to change its sequence to conform to the desired sequence is accomplished by M13 primer extension in accord with generally known methods. Once the gene is cloned, it is digested with the unique restriction enzymes and a plurality of end termini-complementary oligonucleotide cassettes are ligated into the unique sites. The mutagenesis is enormously simplified by this method because all of the oligonucleotides can be synthesized so as to have the same restriction sites, and no synthetic linkers are necessary to create the restriction sites.

The number of commercially available restriction enzymes having sites not present in the gene of interest is generally large. A suitable DNA sequence computer search program simplifies the task of finding potential 5' and 3' unique flanking sites. A primary constraint is that any mutation introduced in creation of the restriction site must be silent to the final constructed amino acid coding sequence. For a candidate restriction site 5' to the target codon a sequence must exist in the gene which contains at least all the nucleotides but for one in the recognition sequence 5' to the cut of the candidate enzyme. For example, the blunt cutting enzyme SmaI (CCC/GGG) would be a 5' candidate if a nearby 5' sequence contained NCC, CNC, or CCN. Furthermore, if N needed to be altered to C this alteration must leave the amino acid coding sequence intact. In cases where a permanent silent mutation is necessary to introduce a restriction site one may want to avoid the introduction of a rarely used codon. A similar situation for SmaI would apply for 3' flanking sites except the sequence NGG, GNG, or GGN must exist. -The criteria for locating candidate enzymes is most relaxed for blunt cutting enzymes and most stringent for 4 base overhang enzymes. In general many candidate sites are available. For the codon-222 target described herein a BalI site (TGG/CCA) could have been engineered in one base pair 5' from the KpnI site. A 3' EcoRV site (GAT/ATC) could have been employed 11 base pairs 5' to the PstI site. A cassette having termini ranging from a blunt end up to a four base-overhang will function without difficulty. In retrospect, this hypothetical EcoRV site would have significantly shortened the oligonucleotide cassette employed (9 and 13 base pairs) thus allowing greater purity and lower pool bias problems. Flanking sites should obviously be chosen which cannot themselves ligate so that ligation of the oligonucleotide cassette can be assured in a single orientation.

The mutation per se need not be predetermined. For example, an oligonucleotide cassette or fragment is randomly mutagenized with nitrosoguanidine or other mutagen and then in turn ligated into the hydrolase gene at a predetermined location.

The mutant carbonyl hydrolases expressed upon transformation of the suitable hosts are screened for enzymes exhibiting desired characteristics, e.g. substrate specificity, oxidation stability, pH-activity profiles and the like.

A change in substrate specificity is defined as a difference between the Kcat/Km ratio of the precursor enzyme and that of the mutant. The Kcat/Km ratio is a measure of catalytic efficiency. Procaryotic carbonyl hydrolases with increased or diminished Kcat/Km ratios are described in the examples. Generally, the objective will be to secure a mutant having a greater (numerically larger) Kcat/Km ratio for a given substrate, thereby enabling the use of the enzyme to more efficiently act on a target substrate. An increase in Kcat/Km ratio for one substrate may be is accompanied by a reduction in Kcat/Km ratio for another substrate. This is a shift in substrate specificity, and mutants exhibiting such shifts have utility where the precursors are undesirable, e.g. to prevent undesired hydrolysis of a particular substrate in an admixture of substrates.

Kcat and Km are measured in accord with known procedures, or as described in Example 18.

Oxidation stability is a further objective which is accomplished by mutants described in the examples. The stability may be enhanced or diminished as is desired for various uses. Enhanced stability is effected by deleting one or more methionine, tryptophan, cysteine or lysine residues and, optionally, substituting another amino acid residue not one of methionine, tryptophan, cysteine or lysine. The opposite substitutions result in diminished oxidation stability. The substituted residue is preferably alanyl, but neutral residues also are suitable.

Mutants are provided which exhibit modified ph-activity profiles. A ph-activity profile is a plot of pH against enzyme activity and may be constructed as illustrated in Example 19 or by methods known in the art. It may be desired to obtain mutants with broader profiles, i.e., those having greater activity at certain pH than the precursor, but no significantly greater activity at any pH, or mutants with sharper profiles, i.e. those having enhanced activity when compared to the precursor at a given pH, and lesser activity elsewhere.

The foregoing mutants preferably are made within the active site of the enzyme as these mutations are most likely to influence activity. However, mutants at other sites important for enzyme stability or conformation are useful. In the case of *Bacillus subtilisin* or its pre, prepro and pro forms, mutations at tyrosine-1, aspartate+32, asparagine+155, tyrosine+104, methionine+222, glycine+166, histidine+64, glycine+169, phenylalanine+189, serine+33, serine+221, tyrosine+217, glutamate+156 and/or alanine+152 produce mutants having changes in the characteristics described above or in the processing of the enzyme. Note that these amino acid position numbers are those assigned to *B. amyloliquefaciens* subtilisin as seen from FIG. 7. It should be understood that a deletion or insertion in the N-terminal direction from a given position will shift the relative amino acid positions so that a residue will not occupy its original or wild type numerical position. Also, allelic differences and the variation among various procaryotic species will result in positions shifts, so that position 169 in such subtilisins will not be occupied by glycine. In such cases the new positions for glycine will be considered equivalent to and embraced within the designation glycine+169. The new position for glycine+169 is readily identified by scanning the subtilisin in question for a region homologous to glycine+169 in FIG. 7.

One or more, ordinarily up to about 10, amino acid residues may be mutated. However, there is no limit to the number of mutations that are to be made aside from commercial practicality.

The enzymes herein may be obtained as salts. It is clear that the ionization state of a protein will be dependent on the pH of the surrounding medium, if it is in solution, or of the solution from which it is prepared, if it is in solid form. Acidic proteins are commonly prepared as, for example, the ammonium, sodium, or potassium salts; basic proteins as the chlorides, sulfates, or Phosphates. Accordingly, the present application includes both electrically neutral and salt forms of the designated carbonyl hydrolases, and the term carbonyl hydrolase refers to the organic structural backbone regardless of ionization state.

The mutants are particularly useful in the food processing and cleaning arts. The carbonyl hydrolases, including mutants, are produced by fermentation as described herein and recovered by suitable techniques. See for example K. Anstrup, 1974, *Industrial Aspects of Biochemistry*, ed. B. Spencer pp. 23–46. They are formulated with detergents or other surfactants in accord with methods known per se for use in industrial processes, especially laundry. In the latter case the enzymes are combined with detergents, builders, bleach and/or fluorescent whitening agents as is known in the art for proteolytic enzymes. Suitable detergents include linear alkyl benzene sulfonates, alkyl ethoxylated sulfate, sulfated linear alcohol or ethoxylated linear alcohol. The compositions may be formulated in granular or liquid form. See for example U.S Pat. Nos. 31623,957; 4,404,128; 4,381,247; 4,404,115; 4,318,818; 4,261,868; 4,242,219; 4,142,999; 4,111,855; 4,011,169; 4,090,973; 3,985,686; 3,790,482; 3,749,671; 3,560,392; 3,558,498; and 3,557,002.

The following disclosure is intended to serve as a representation of embodiments herein, and should not be construed as limiting the scope of this application.

GLOSSARY OF EXPERIMENTAL MANIPULATIONS

In order to simplify the Examples certain frequently occurring methods will be referenced by shorthand phrases.

Plasmids are designated by a small p preceeded and/or followed by capital letters and/or numbers. The starting plasmids herein are commercially available, are available on an unrestricted basis, or can be constructed from such available plasmids in accord with Published procedures.

"Klenow treatment" refers to the process of filling a recessed 3' end of double stranded DNA with deoxyribonucleotides complementary to the nucleotides making up the protruding 5' end of the DNA strand. This process is usually used to fill in a recessed end resulting from a restriction enzyme cleavage of DNA. This creates a blunt or flush end, as may be required for further legations. Treatment with Klenow is accomplished by reacting (generally for 15 minutes at 15° C.) the appropriate complementary deoxyribonucleotides with the DNA to be filled in under the catalytic activity (usually 10 units) of the Klenow fragment of *E. coli* DNA polymerase I ("Klenow"). Klenow and the other reagents needed are commercially available. The procedure has been published extensively. See for example T. Maniatis et al., 1982, *Molecular Cloning*, pp. 107–108.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the nicroorganism from which each restriction enzyme originally was obtained. In general, about 1 $\mu$g of plasmid or DFJA fragment is used with about 1 unit of enzyme in about 20 $\mu$l of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for depliosphorylation are conventional (T. Maniatis et al., Id., pp. 133–134).

"Recovery" or "isolation" of a given fragment of DNA from a restriction digest means separation of the digest on 6 percent polyacrylamide gel electrophoresis, identification of the fragment of interest by molecular weight (using DNA fragments of known molecular weight as markers), removal of the gel section containing the desired fragment, and separation of the gel from DNA. This procedure is known generally. For example, see R. Lawn et al., 1981, "Nucleic Acids Res." 9:6103–6114, and D. Goeddel et al., (1980) "Nucleic Acids Res." 8:4057.

"Southern Analysis" is a method by which the presence of DNA sequences in a digest or DNA-containing composition is confirmed by hybridization to a known, labelled oligonucleotide or DNA fragment. For the purposes herein, Southern analysis shall mean separation of digests on 1 percent agarose and depurination as described by G. Wahl et al., 1979, "Proc. Nat. Acad.

Sci. U.S.A." 76:3683-3687, transfer to nitrocellulose by the method of E. Southern, 1975, "J. Mol. Biol." 98:503-517, and hybridization as described by T. Maniatis et al., 1978, "Cell" 15:687-701.

"Transformation" means introducing DNA into an organism so that the DNA is replicable, either as an extrachromosomal element or chromosomal integrant. Unless otherwise stated, the method used herein for transformation of *E. coli* is the $CaCl_2$ method of Mandel et al., 1970, "J. Mol. Biol." 53:154, and for Bacillus, the method of Anagnostopolous et al., 1961, "J. Bact." 81:791-746.

"Ligation" refers to the process of forming phosphodiester bonds between two double stranded nucleic acid fragments (T. Maniatis et al., Id., p. 146). Unless otherwise stated, ligation was accomplished using known buffers and conditions with 10 units of T4 DNA ligase ("ligase") per 0.5 μg of approximately equimolar amounts of the DNA fragments to be ligated. Plasmids from the transformants were prepared, analyzed by restriction mapping and/or sequenced by the method of Messing, et al., 1981, "Nucleic Acids Res.", 9:309.

"Preparation" of DNA from transformants means isolating plasmed DNA from microbial culture. Unless otherwise stated, the alkaline/SDS method of Maniatis et al., Id. p. 90., was used.

"Oligonucleotides" are short length single or double stranded polydeoxynucleotides which were chemically synthesized by the method of Crea et al., 1980, "Nucleic Acids Res." 8:2331-2348 (except that mesitylene nitrotriazole was used as a condensing agent) and then purified on polyacrylamide gels.

All literature citations are expressly incorporated by reference.

EXAMPLE 1

Preparation of a Genomic DNA Library from *B. amyloliquifaciens* and Isolation of its Subtilisin Gene The known amino acid sequence of the extracellular *B. amyloliquefaciens* permits the construction of a suitable probe mixture. The sequence of the mature subtilisin is included (along with the additional information contributed by the present work) in FIG. 1. All codon ambiguity for the sequence of amino acids at position.117 through 121 is covered by a pool of eight oligonucleotides of the sequence

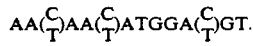

Chromosomal DNA isolated from *B. amyloliquefaciens* (ATCC No. 23844) as described by J. Marmur, "j. Mol, Biol.", 3:208, was partially digested by Sau 3A, and the fragments size selected and ligated into the BamH I site of dephosphorylated pBS42. (pBS42 is a shuttle vector containing origins of replication effective both in *E. coli* and Bacillus. It is prepared as described in Example 4.) The Sau3A fragment containing vectors were transformed into *E. coli* K12 strain 294 (ATCC No. 31446) according to the method of M. Mandel, et al., 1970, "J. Mol. Bio." 53: 154 using 80–400 nanograms of library DNA per 250 μL of competent cells.

Cells from the transformation mixture were plated at a density of $1-5 \times 10^3$ transformants per 150 mm plate containing LB medium +12.5 μg/ml chloramphenicol and grown overnight at 37° C. until visible colonies appeared. The plates were then replica plated onto BA85 nitrocellulose filters overlayed on LB/chloramphenicol plates. The replica plates were grown 10-12 hours at 37° C. and the filters transferred to fresh plates containing LB and 150 μg/ml spectinomycin to amplify the plasmid pool.

After overnight incubation at 37° C., filters were processed essentially as described by Grunstein and Hogness, 1975, "Proc. Natl. Acad. Sci. (USA)" 72: 3961. Out of approximately 20,000 successful transformants, 25 Positive colonies were found. Eight of these positives were streaked to purify individual clones. 24 clones from each streak were grown in microtiter wells, stamped on to two replica filters, and probed as described above with either

or

which differ by only one nucleotide. As shown in FIG. 2, pool 1 hybridized to a much greater extent to all positive clones than did pool 2, suggesting specific hybridization.

Figure 3:
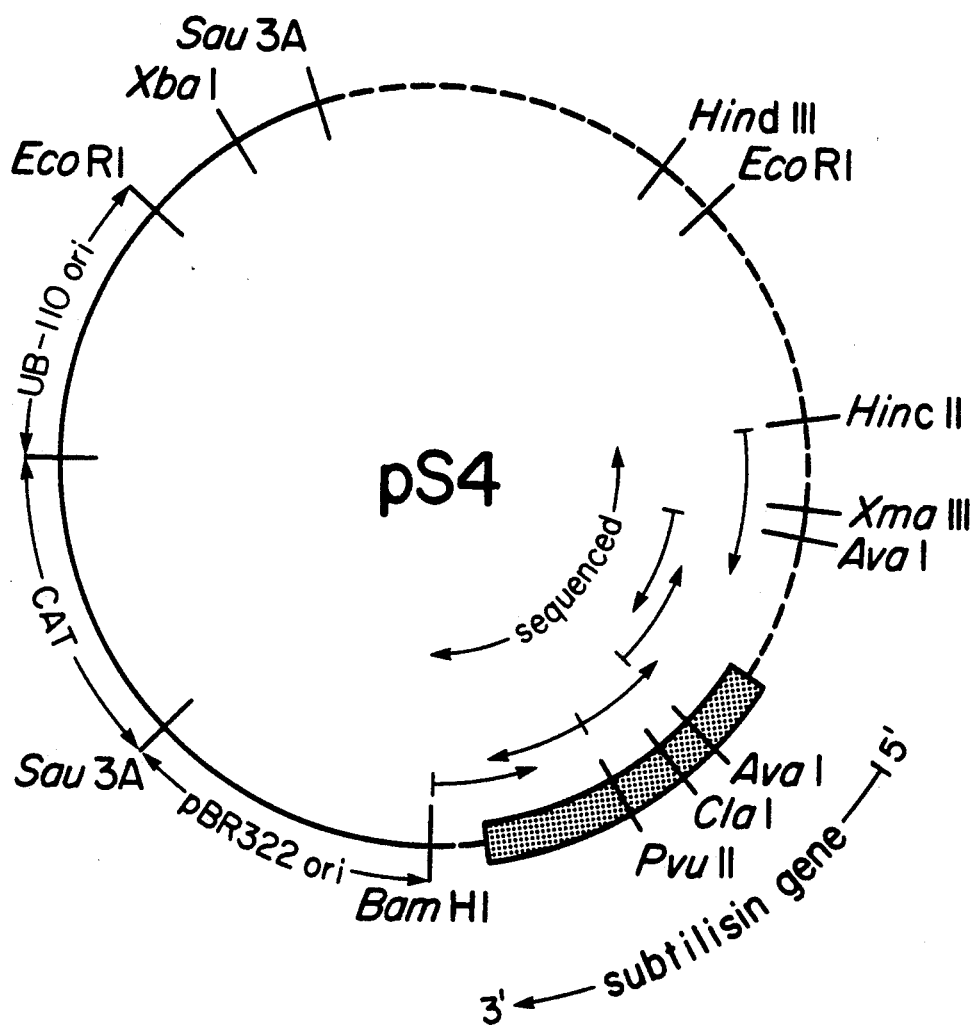
FIG. 3 shows the restriction analysis of the subtilisin expression plasmid (pS4). pBS42 vector sequences (4.5 kb) are shown in solid while the insert sequence (4.4 kb) is shown dashed.

Four out of five miniplasmid preparations (Maniatis et al., Id.) from positive clones gave identical restriction digest patterns when digested with Sau3A or HincII. The plasmid isolated from one of these four identical colonies by the method of Maniatis et al., Id., had the entire correct gene sequence and was designated pS4. The characteristics of this plasmid as determined by restriction analysis are shown in FIG. 3.

EXAMPLE 2

Expression of the Subtilism Gene

*Bacillus subtilis* I-168 (Catalog No. 1-A1, Bacillus Genetic Stock Center) was transformed with pS4 and and a single chloramphenicol resistant transformant then grown in minimal medium. After 24 hours, the culture was centrifuged and both the supernatant (10-200 μl) and pellet assayed for proteolytic activity by measuring the change in absorbance per minute at 412 nm using 1 ml of the chromogenic substrate succinyl-L-a¹a-ala-pro-phe-p-nitroanilide (0.2 μM) in 0.1 M sodium phosphate (pH 8.0) at 25° C. A *B. subtilis* I-168 culture transformed with pBS42 used as a control showed less than 1 1200 of the activity shown by the pS4 transformed culture. Greater than 95 percent of the protease activity of the pS4 culture was present in the supernatant, and was completely inhibited by treatment with phenylmethylsulfonyl fluoride (PMSF) but not by EDTA.

Figure 4:
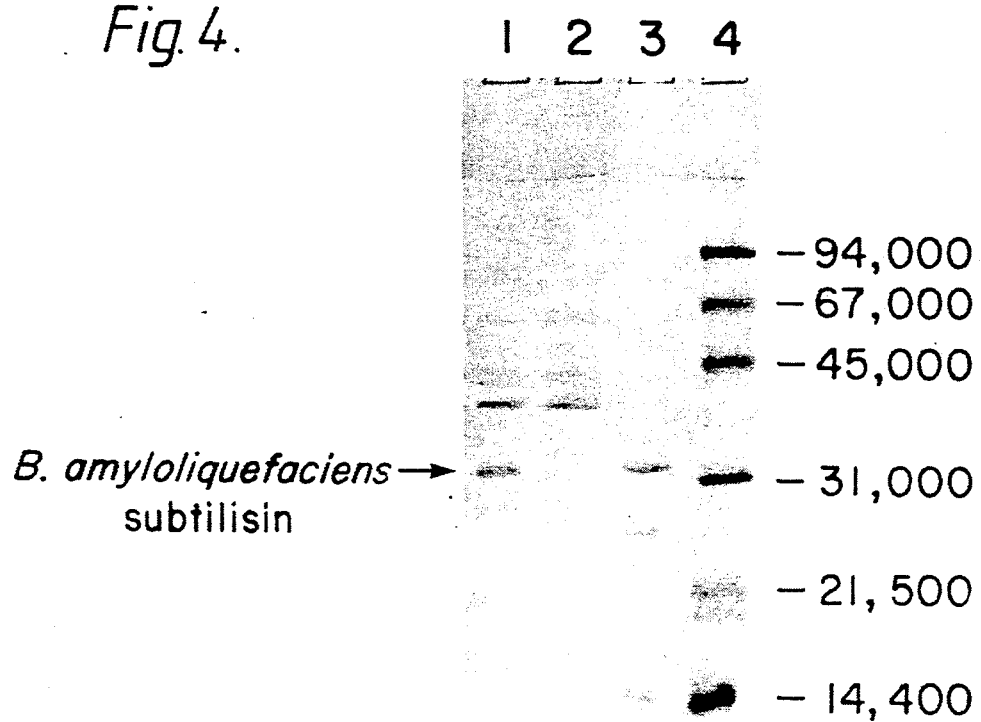
FIG. 4 shows the results of SDS-PAGE performed on supernatants from cultures transformed with pBS42 and pS4.

Aliquots of the supernatants were treated with PMSF and EDTA to inhibit all protease activity and analyzed by 12 percent SDS-PAGE according to the method of Laemmli, U.K., 1970 "Nature", 227: 680. To prepare the supernatants, 16 μL of supernatant was treated with 1 mM PMSF, 10 mM EDTA for 10 minutes, and boiled with 4 μL of 5× concentrated SDS sample buffer minus β-mercaptoethanol. The results of Coomassie stain on runs using supernatants of cells transformed with pS4, pBS42, and untransformed *B. amyloliquefaciens* are shown in FIG. 4. Lane 3 shows authentic subtilisin from *B. amyloliquefaciens*. Lane 2 which is the supernatant from pBS42 transformed *B. subtilis,* does not give the 31,000 MW band associated with subtilisin which is exhibited by Lane I from pS4 transformed hosts. The approximately 31,000 VW band result for subtilisin is characteristic of the slower mobility shown by the known M.W. 27,500 subtilisin preparations in general.

EXAMPLE 3

Sequencing of the B. amyloliquefaciens Subtilism Gene

The entire sequence of an EcoRI-BamHI fragment (wherein the EcoRI site was constructed by conversion of the HincII site) of pS4 was determined by the method of F. Sanger, 1977, "Proc. Natl. Acad. Sci (USA)", 74:5463. Referring to the restriction map shown in FIG. 3, the BamHI-PvuII fragment was found to hybridize with pool 1 oligonucleotides by Southern analysis. Data obtained from sequencing of this fragment directed the sequencing of the remaining fragments (e.g. PvuII-HincII and AvaI-AvaI). The results are shown in FIG. 1.

Examination of the sequence confirms the presence of codons for the mature subtilisin corresponding to that secreted by the B. amyloliquefaciens. Immediately upstream from this sequence is a series of 107 codons beginning with the GTG start codon at −107. Codon −107 to approximately codon −75 encodes an amino acid sequence whose characteristics correspond to that of known signal sequences. (Most such signal sequences are 18-30 amino acids in length, have hydrophobic cores, and terminate in a small hydrophobic amino acid.) Accordingly, examination of the sequence data would indicate that codons −107 to approximately −75 encode the signal sequence; the remaining intervening codons between −75 and −1 presumably encode a prosequence.

EXAMPLE 4

Figure 5:
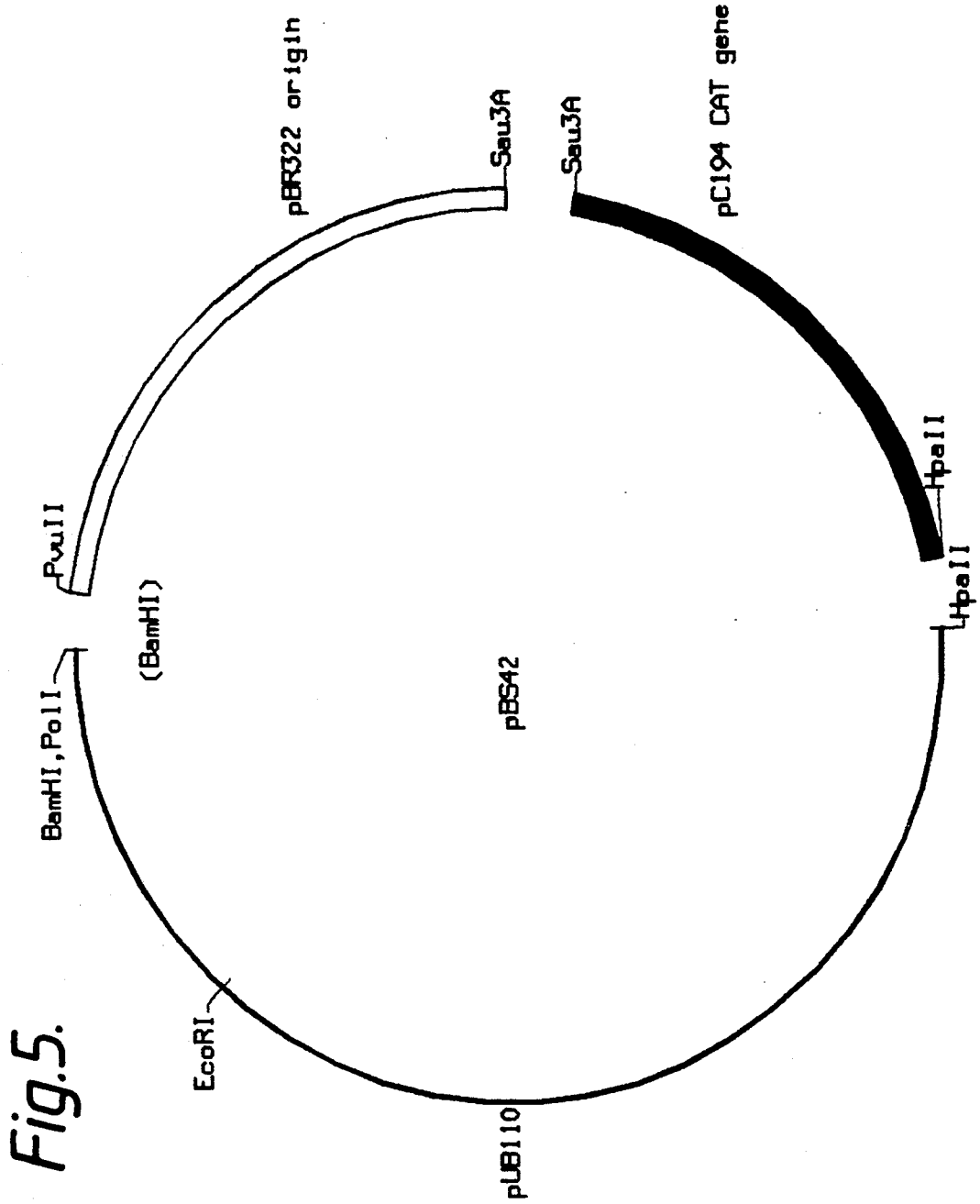
FIG. 5 shows the construction of the shuttle vector pBS42.

Construction of pBS42 pBS42 is formed by three-way ligation of fragments derived from PUB110, pC194, and pBR322 (see FIG. 5). The fragment from PUB110 is the approximately 2600 base pair fragment between the HpaII site at 1900 and the BamHI site at 4500 and contains an origin of replication operable in Bacillus: T. Grycztan, et al., 1978 "J. Bacteriol.", 134: 318 (1978); A. Jalanko, et al., 1981 "Gene", 14: 325. The BamHI site was tested with Klenow. The pBR322 portion is the 1100 base pair fragment between the PvuII site at 2067 and the Sau3A site at 3223 which contains the E. coli origin of replication: F. Bolivar, et al., 1977 "Gene", 2: 95; J. Sutcliffe, 1978, *Cold Spring Harbor Symposium* 43: I, 77. The pC194 fragment is the 1200 base pair fragment between the HpaII site at 973 and the Sau3A site at 2006 which contains the gene for chloramphenicol resistance expressible in both E. coli and B. subtilis: S. Ehrlich, "Proc. Natl. Acad. Sci. (USA)", 74:1680; S. Horynuchi et al., 1982, "J. Bacteriol." 150: 815.

pBS42 thus contains origins of replication operable both in E. coli and in Bacillus and an expressible gene for chloramphenicol resistance.

EXAMPLE 5

Isolation and Sequencing of the B. subtilis Subtilisin Gene

B. subtilis I168 chromosomal DNA was digested with EcoRI and the fragments resolved on gel electrophoresis. A single 6 kb fragment hybridized to a [α-$^{32}$P] CTP nick translation—labelled fragment obtained from the C-terminus of the subtilisin structural gene in pS4, described above. The 6 kb fragment was electroluted and ligated into pBS42 which had been digested with EcoRI and treated with bacterial alkaline phosphatase. E. coli ATCC 31446 was transformed with the ligation mixture and transformants selected by growth on LB agar containing 12.5 pg chloramphenicol/ml. Plasmid DNA was prepared from a pooled suspension of 5,000 transformed colonies. This DNA was transformed into B. subtilis BG84, a protease deficient strain, the preparation of which is described in Example 8 below. Colonies which produced protease were screened by plating on LB agar plus 1.5 percent w/w Carnation powdered nonfat skim milk and 5 μg chloramphenicol/ml (hereafter termed skim milk selection plates) and observing for zones of clearance evidencing proteolytic activity.

Plasmid DNA was prepared from protease producing colonies, digested with EcoRI, and examined by Southern analysis for the presence of the 6 kb EcoRI insert by hybridization to the $^{32}$P-labelled C-terminus fragment of the subtilisin structural gene from B. amyloliquefaciens. A positive clone was identified and the plasmid was designated pS168.1. B. subtilis BG84 transformed with PS168.1 excreted serine protease at a level 5-fold over that produced in B. subtilis I168. Addition of EDTA to the supernatants did not affect the assay results, but the addition of PMSF (phenylmethylsufonyl fluoride) to the supernatants reduced protease activity to levels undetectable in the assay described in Example 8 for strain BG84.

Figure 6:
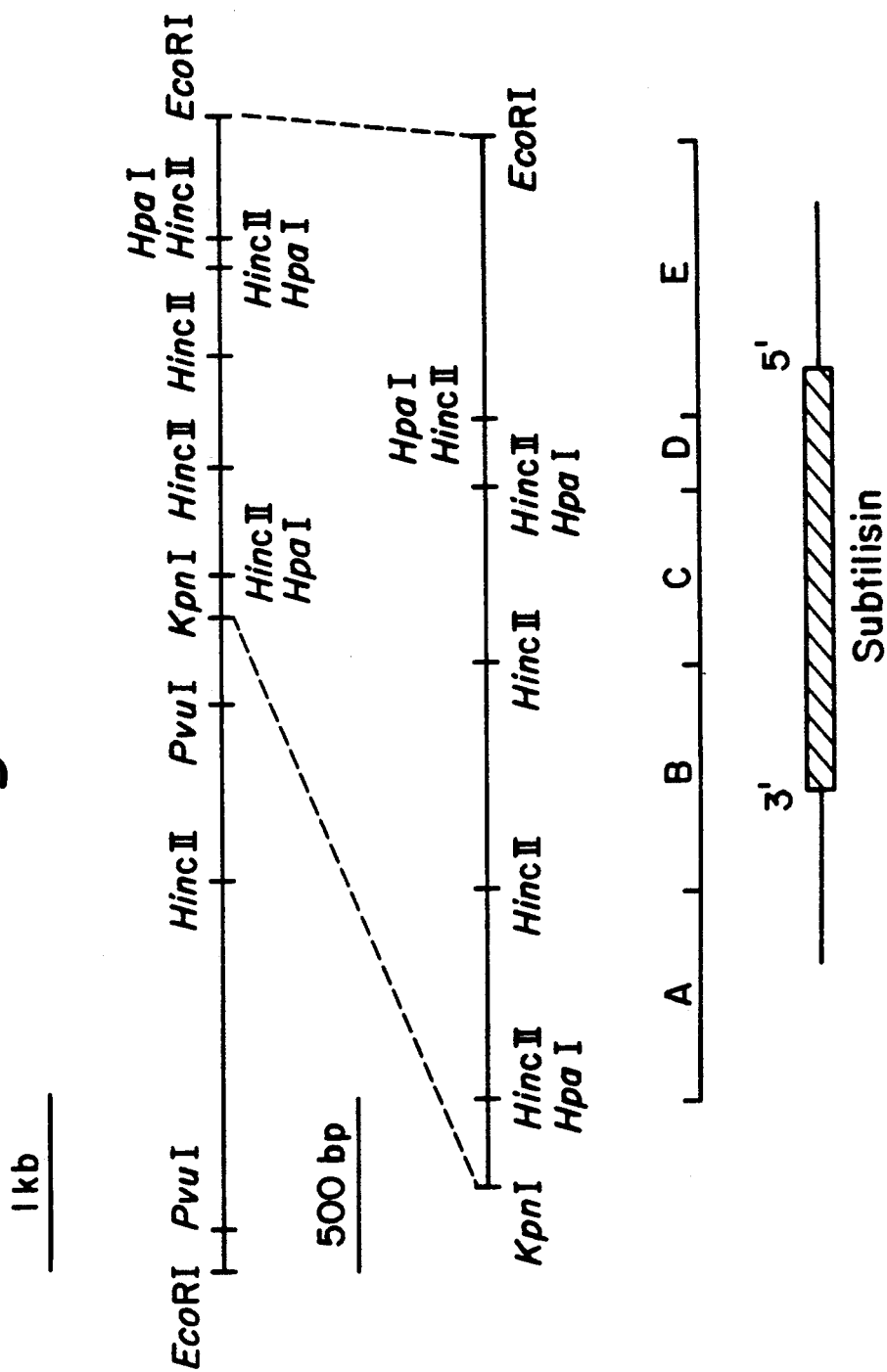
FIG. 6 shows a restriction map for a sequence including the B. subtilis subtilisin gene.

A restriction map of the 6.5 kb EcoRI insert is shown in FIG. 6. The subtilisin gene was localized to within the 2.5 kb KpnI-EcoRI fragment by subcloning various restriction enzyme digests and testing for expression of subtilisin in B. subtilis BG84. Southern analysis with the labelled fragment from the C-terminus of the B. amyloliquefaciens subtilisin gene as a probe localized the C-terminus of the B. subtilis gene to within or part of the 631 bp HincII fragment B in the center of this subclone (see FIG. 6). The tandem HincII fragments B, C, and D and HincII-EcoRI fragment E (FIG. 6) were ligated into the M13 vectors mp8 or mp9 and sequenced in known fashion (J. Messing et al., 1982, "Gene" 19:209-276) using dideoxy chain termination (F. Sanger et al., 1977, "Proc. Nat. Acad. Sci. U.S.A." 74:5463-5467). The sequence of this region is shown in FIG. 7. The first 23 amino acids are believed to be a signal peptide. The remaining 83 amino acids between the signal sequence and the mature coding sequence constitute the putative "pro" sequence. The overlined nucleotides at the 3' end of the gene are believed to be transcription terminator regions. Two possible Shine-Dalgarno sequences are underlined upstream from the mature start codon.

EXAMPLE 6

Manufacture of an Inactivating Mutation of the B. subtilis Subtilism Gene

Figure 8:
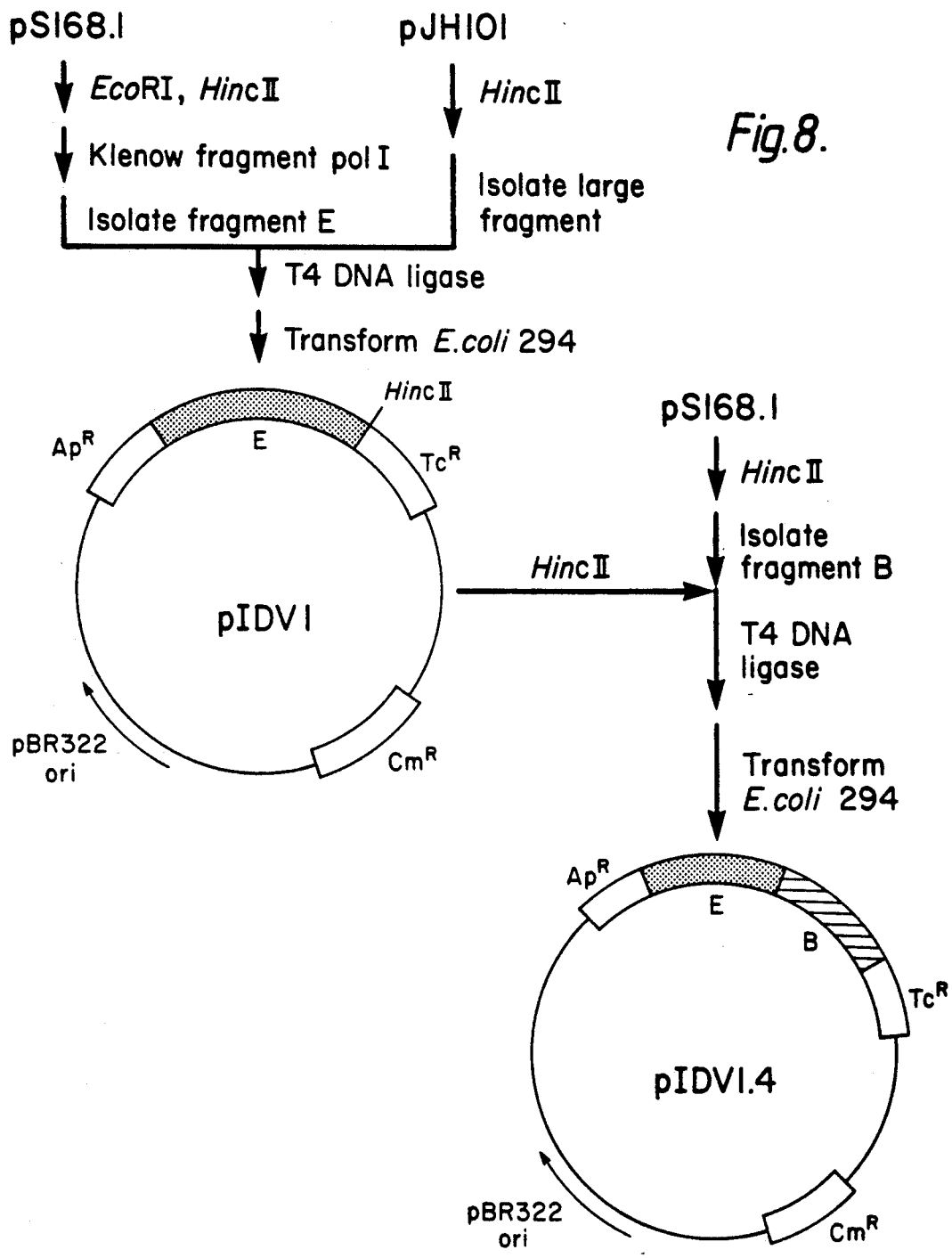
FIG. 8 demonstrates a construction method for obtaining a deletion mutant of a B. subtilis subtilisin gene.

A two step ligation, shown in FIG. 8, was required to construct a plasmid carrying a defective gene which would integrate into the Bacillus chromosome. In the first step, pS168.1, which contained the 6.5 kb insert originally recovered from the B. subtilis genomic library as described in Example 5 above, was digested with EcoRI, the reaction products treated with Klenow, the DNA digested with HincII, and the 800 bp EcoRI-HincII fragment E (see FIG. 6) that contains, in part, the 5' end of the B. subtilis subtilisin gene, was recovered. This fragment was ligated into pJH101

(pJH101 is available from J. Hoch (Scripps) and is described by F. A. Ferrari et al., 1983, "J. Bact." 134:318-329) that had been digested with HincII and treated with bacterial alkaline phosphotase. The resultant plasmid, pIDV1, contained fragment E in the orientation shown in FIG. 8. In the second step, pS168.1 was digested with HincII and the 700 bp HincII fragment B, which contains the 3' end of the subtilisin gene, was recovered. pIDV1 was digested at its unique HincII site and fragment B ligated to the linearized plasmid, transformed in E. coli ATCC 31,446, and selected on LB plates containing 12.5 μg chloramphenicol/ml or 20 pg ampicillin/ml. One resulting plasmid, designated pIDV1.4, contained fragment B in the correct orientation with respect to fragment E. This plasmid pIDV1.4, shown in FIG. 8, is a deletion derivative of the subtilisin gene containing portions of the 5' and 3' flanking sequences as well.

B. subtilis BG77, a partial protease-deficient mutant (Prt±) prepared in Example 8 below was transformed with pIDV1.4. Two classes of chloramphenicol resistant (Cm$^r$) transformants were obtained. Seventy-five percent showed the same level of proteases as BG77 (Prt±) and 25 percent were almost completely protease deficient (Prt−) as observed by relative zones of clearing on plates containing LB agar plus skim milk. The Cm$^r$ Prt− transformants could not be due to a single crossover integration of the plasmid at the homologous regions for fragment E or B because, in such a case, the gene would be uninterrupted and the phenotype would be Prt±. In fact, when either of fragments E or B were ligated independently into pJH101 and subsequently transformed into B. subtilis BG77, the protease deficient phenotype was not observed. The Cm$^r$ phenotype of Cm$^r$ Prt− pIDV1.4 transformants was unstable in that Cm$^s$ Prt− derivatives could be isolated from Cm$^r$ Prt− cultures at a frequency of about 0.1 percent after 10 generations of growth in minimal medium in the absence of antibiotic selection. One such derivative was obtained and designated BG2018. The deletion was transferred into IA84 (a BGSC strain carrying two auxotrophic mutations flanking the subtilisin gene) by PBS1 transduction. The derivative organism was designated BG2019.

EXAMPLE 7

Preparation of a Genomic DNA Library from B. subtilis and Isolation of its Neutral Protease Gene The partial amino acid sequence of a neutral protease of B. subtilis is disclosed by P. Levy et al. 1975, "Proc. Nat. Acad. Sci. USA" 72:4341-4345. A region of the enzyme (Asp Gln Met Ile Tyr Gly) was selected from this published sequence in which the least redundancy existed in the potential codons for the amino acids in the region. 24 combinations were necessary to cover all the potential coding sequences, as described below.

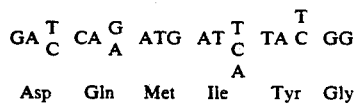

Four pools, each containing six alternatives, were prepared as described above in Example 1. The pools were labelled by phosphorylization with [γ-$^{32}$p] ATP.

The labelled pool containing sequences conforming closest to a unique sequence in a B. subtilis genome was selected by digesting B. subtilis (1A72, Bacillus Genetic Stock Center) DNA with various restriction enzymes, separating the digests on an electrophoresis gel, and hybridizing each of the four probe pools to each of the blotted digests under increasingly stringent conditions until a single band was seen to hybridize. Increasingly stringent conditions are those which tend to disfavor hybridization, e.g., increases in formamide concentration, decreases in salt concentration and increases in temperature. At 37° C. in a solution of 5×Denhardt's, 5×SSC, 50 mM NAPO$_4$ pH 6.8 and 20 percent formamide, only pool 4 would hybridize to a blotted digest. These were selected as the proper hybridization conditions to be used for the neutral protease gene and pool 4 was used as the probe.

A lambda library of B. subtilis strain BGSC 1-A72 was prepared in conventional fashion by partial digestion of the Bacillus genomic DNA by Sau3A, separation of the partial digest by molecular weight on an electrophoresis gel, elution of 15-20 kb fragments (R. Lawn et al., 1981, "Nucleic Acids Res." 9:6103-6114), and ligation of the fragments to BamHI digested charon 30 phage using a Packagene kit from Promega Biotec.

E. coli DP50supF was used as the host for the phage library, although any known host for Charon lambda phage is satisfactory. The E. coli host was plated with the library phage and cultured, after which plaques were assayed for the presence of the neutral protease gene by transfer to nitrocellulose and screening with probe pool 4 (Benton and Davis, 1977, "Science" 196:180-182). Positive plaques were purified through two rounds of single plaque purification, and two plaques were chosen for further study, designated λNPRG1 and λNPRG2. DNA was prepared from each phage by restriction enzyme hydrolysis and separation on electrophoresis gels. The separated fragments were blotted and hybridized to labelled pool 4 oligonucleotides. This disclosed that λNPRG1 contained a 2400 bp HindIII hybridizing fragment, but no 4300 EcoRI fragment, while λNPRG2 contained a 4300 bp EcoRI fragment, but no 2400 bp HindIII fragment.

The 2400 bp λNPRG1 fragment was subcloned into the HindIII site of pJH101 by the following method. λNPRG1 was digested by HindIII, the digest fractionated by electrophoresis and the 2400 bp fragment recovered from the gel. The fragment was ligated to alkaline phosphatase-treated HindIII digested pjH101 and the ligation mixture used to transform E. coli ATCC 31446 by the calcium chloride shock method of V. Hershfield et al., 1974, "Proc. Nat. Acad. Sci. (U.S.A.)" 79:3455-3459). Transformants were identified by selecting colonies capable of growth on plates containing LB medium plus 12.5 μg chloramphenicol/ml.

Transformant colonies yielded several plasmids. The orientation of the 2400 bp fragment in each plasmid was determined by conventional restriction analysis (orientation is the sense reading or transcriptional direction of the gene fragment in relation to the reading direction of the expression vector into which it is ligated.) Two plasmids with opposite orientations were obtained and designated pNPRsubH6 and pNPRsubH1.

The 4300 bp EcoRI fragment of λNPRG2 was subcloned into pBR325 by the method described above for the 2400 bp fragment except that λNPRG2 was digested with EcoRI and the plasmid was alkaline phosphatase-treated EcoRI-digested pBR325. pBR325 is described by F. Bolivar, 1978, "Gene" 4:121-136. Two plasmids were identified in which the 4300 bp insert was present in different orientations. These two plasmids were designated pNPRsubRI and pNPRsubRIb.

EXAMPLE 8

Characterization of *B. subtilis* Neutral Protease Gene

Figure 9:
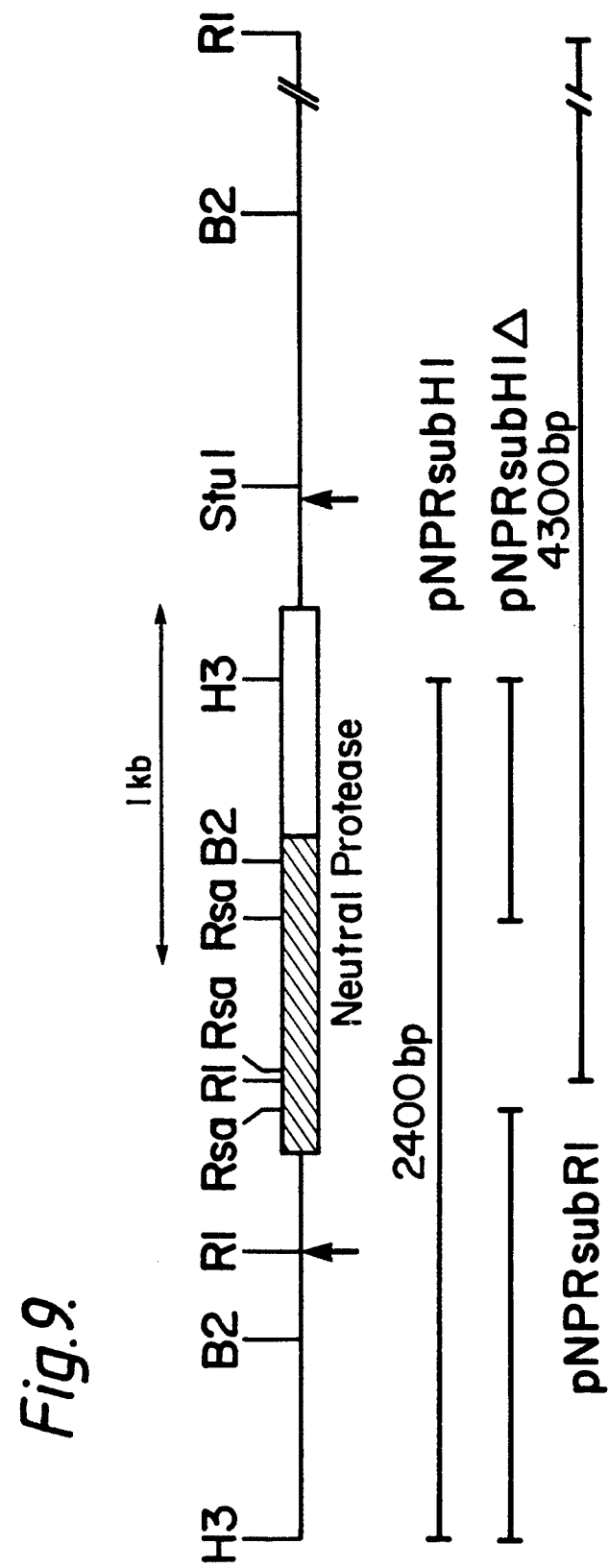
FIG. 9 discloses the restriction map for a B. subtilis neutral protease gene.

The pNPRsubH1 insert was sequentially digested with different restriction endonucleases and blot hybridized with labelled pool 4 in order to prepare a restriction map of the insert (for general procedures of restriction mapping see T. Maniatis et al., Id., p. 377). A 430 bp RsaI fragment was the smallest fragment that hybridized to probe pool 4. The RsaI fragment was ligated into the SmaI site of M13 mp8 (J. Messing et al., 1982, "Gene" 19:269-276 and J. Messing in *Methods in Enzymology*, 1983, R. Wu et al., Eds., 101:20-78) and the sequence determined by the chain-terminating dideoxy method (F. Sanger et al., 1977, "Proc. Nat. Acad. Sci. U.S.A." 74:5463-5467). Other restriction fragments from the pNPRsubH1 insert were ligated into appropriate sites in M13 mp8 or M13 mp9 vectors and the sequences determined. As required, dITP was used to reduce compression artifacts (D. Mills et al., 1979, "Proc. Nat. Acad. Sci. (U.S.A.)" 76:2232-2235). The restriction map for the pNPRsubH1 fragment is shown in FIG. 9. The sequences of the various fragments from restriction enzyme digests were compared and an open reading frame spanning a codon sequence translatable into the amino and carboxyl termini of the protease (P. Levy et al., Id.) was determined. An open reading frame is a DNA sequence commencing at a known point which in reading frame (every three nucleotides) does not contain any internal termination codons. The open reading frame extended past the amino terminus to the end of the 2400 bp HindIII fragment. The 1300 bp BglII - HindIII fragment was prepared from pNPRsubRIb (which contained the 4300 bp EcoRI fragment of λNPRG2) and cloned in M13 mp8. The sequence of this fragment, which contained the portion of the neutral protease leader region not encoded by the 2400 bp fragment of pNPRsubH1, was determined for 400 nucleotides upstream from the HindIII site.

The entire nucleotide sequence as determined for this neutral protease gene, including the putative secretory leader and prepro sequence, are shown in FIG. 10. The numbers above the line refer to amino acid positions. The underlined nucleotides in FIG. 10 are believed to constitute the ribosome binding (Shine-Dalgarno) site, while the overlined nucleotides constitute a potential hairpin structure presumed to be a terminator. The first 27-28 of the deduced amino acids are believed to be the signal for the neutral protease, with a cleavage point at ala-27 or ala-28. The "pro" sequence of a proenzyme structure extends to the amino-terminal amino acid (ala-222) of the mature, active enzyme.

A high copy plasmid carrying the entire neutral protease gene was constructed by (FIG. 11) ligating the BglII fragment of pNPRsubR1, which contains 1900 bp (FIG. 9), with the PvuII - HindIII fragment of pNPRsubH1, which contains 1400 bp . pBS42 (from Example 4) was digested with BamHI and treated with bacterial alkaline phosphatase to prevent plasmid recircularization. pNPRsubR1 was digested with BglII, the 1900 bp fragment was isolated from gel electrophoresis and ligated to the open BamHI sites of pBS42. The ligated plasmid was used to transform *E. coli* ATCC 31446 by the calcium chloride shock method (V. Hershfield et al., Id.), and transformed cells selected by growth on plates containing LB medium with 12.5 µg/ml chloramphenicol. A plasmid having the Bgl II fragment in the orientation shown in FIG. 11 was isolated from the transformants and designated pNPRsubB1. pNPRsubB1 was digested (linearized) with EcoRI, repaired to flush ends by Klenow treatment and then digested with HindIII. The larger fragment from the HindIII digestion (containing the sequence coding for the amino terminal-and upstream regions) was recovered.

Figure 11:
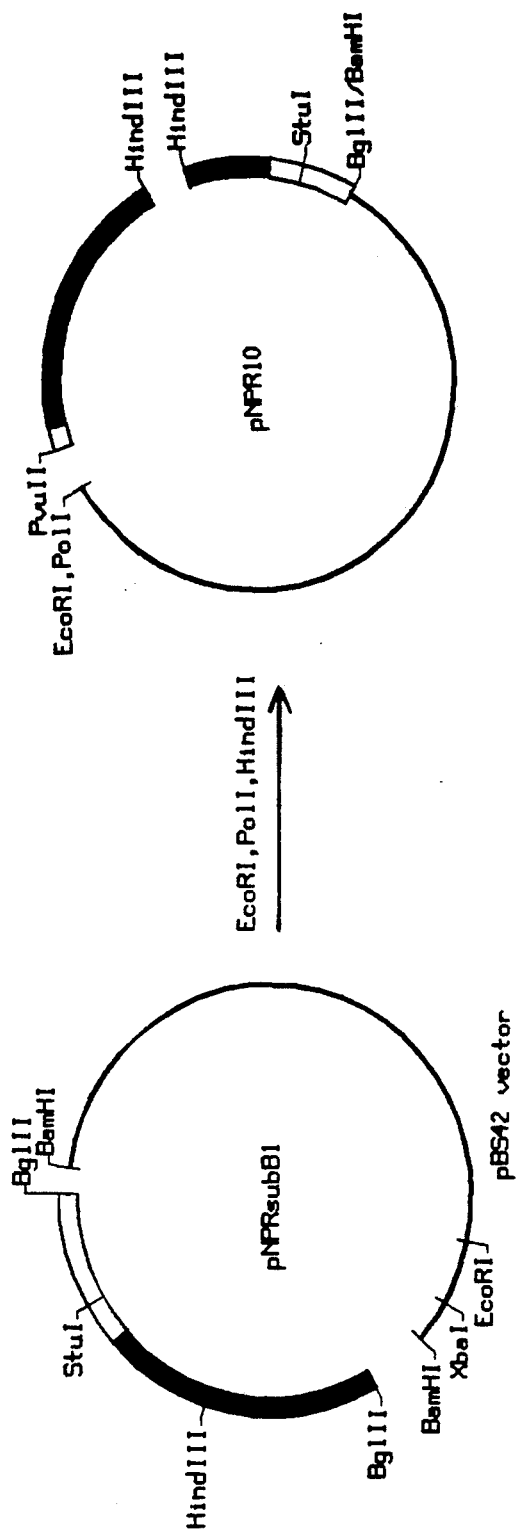
FIG. 11 demonstrates the construction of a vector containing a B. subtilis neutral protease gene.

The carboxyl terminal region of the gene was supplied by a fragment from pNPRsubH1, obtained by digestion of pNPRsubH1 with PvuII and HindIII and recovery of the 1400 bp fragment. The flush end PvuII and the HindIII site of the 1400 bp fragment was ligated, respectively, to the blunted EcoRI and the HindIII site of pNPRsubB1, as shown in FIG. 11. This construct was used to transform *B. subtilis* strain BG84 which otherwise excreted no proteolytic activity by the assays described below. Transformants were selected on plates containing LB medium plus 1.5 percent carnation powdered nonfat milk and 5 µg/ml chloramphenicol. Plasmids from colonies that cleared a large halo were analyzed. Plasmid pNPR10, incorporating the structural gene and flanking regions of the neutral protease gene, was determined by restriction analysis to have the structure shown in FIG. 11.

*B. subtilis* strain BG84 was produced by N-methyl-N'-nitro-N-nitrosoguanidine (NTG) mutagenesis of *B. subtilis* I168 according to the general technique of Adelberg et al., 1965, "Biochem. Biophus. Res. Commun." 18:788-795. Mutagenized strain I168 was plated on skim milk plates (without antibiotic). Colonies producing a smaller halo were picked for further analysis. Each colony was characterized for protease production on skim milk plates and amylase production on starch plates. One such isolate, which was partially protease deficient, amylase positive and capable of sporulation, was designated BG77. The protease deficiency mutation was designated prt-77. The prt-77 allele was moved to a spoOA background by congression as described below to produce strain BG84, a sporulation deficient strain.

TABLE A

| Strain | Relevant Genotype | origin |
|---|---|---|
| I168 | trpC2 | |
| JH703 | trpC2, pheA12, spoOAΔ677 | Trousdale et al.[a] |
| BG16 | purB6, metB5, leuA8, lys-21, hisA, thr-5, sacA321 | Pb 1665 |
| BG77 | trpC2, prt-77 | NTG × I168 |
| BG81 | metB5, prt-77 | BG16 DNA × BG77 |
| BG84 | spoOAΔ677, prt-77 | JH703 DNA × BG81 |

[a]"Mol. Gen. Genetics" 173:61 (1979)

BG84 was completely devoid of protease activity on skim milk plates and does not produce detectable levels of either subtilisin or neutral protease when assayed by measuring the change in absorbance at 412 nm per minute upon incubation with 0.2 µg/ml succinyl (-L-ala-L-ala-L-pro-L-phe) p-nitroanilide (Vega) in 0.1M sodium phosphate, pH 8, at 25° C.. BG84 was deposited in the ATCC as deposit number 39382 on Jul. 21, 1983. Samples for subtilisin assay were taken from late logarithmic growth phase supernatants of cultures grown in modified Schaeffer's medium (T. Leighton et al., 1971, "J. Biol. Chem." 246:3189-3195).

EXAMPLE 9

Expression of the Neutral Protease Gene

BG84 transformed with pNPR10 was inoculated into minimal media supplemented with 0.1 percent casein hydrolysate and 10 μg chloramphenicol and cultured for 16 hours. 0.1 ml of culture supernatant was removed and added to a suspension of 1.4 mg/ml Azocoll proteolytic substrate (Sigma) in 10 mM Tris-HCJ, 100 n#4 NaCl PH 6.8 and incubating with agitation. Undigested substrate was removed by centrifugation and the optical density read at 505 nm. Background values of an Azocoll substrate suspension were subtracted. The amount of protease excreted by a standard protease-expressing strain, BG16 was used to establish an arbitrary level of 100. The results with BG16, and with BG84 transformed with control and neutral protease gene-containing plasmids are shown in Table B in Example 12 below. Transformation of the excreted protease-devoid B. subtilis strain BG84 results in excretion of protease activity at considerably greater levels than in BG16, the wild-type strain.

EXAMPLE 10

Manufacture of an Inactivating Mutation of the Neutral Protease Gene

The two RsaI bounded regions in the 2400 bp insert of pNPRsubH1, totalling 527 bp, can be deleted in order to produce an incomplete structural gene. The translational products of this gene are enzymatically inactive. A plasmid having this deletion was constructed as follows. pJH101 was cleaved by digestion with HindIII and treated with bacterial alkaline phosphatase. The fragments of the neutral protease gene to be incorporated into linearized pJH101 were obtained by digesting pNPRsubH1 with HindIII and RsaI, and recovering the 1200 bp HindIII-RsaI and 680 bp RsaI-HindIII fragments by gel electrophoresis. These fragments were ligated into linearized pJH101 and used to transform E. coli ATCC 31446. Transformants were selected on plates containing LB medium and 20 μg ampicillin/ml. Plasmids were recovered from the transformants and assayed by restriction enzyme analysis to identify a plasmid having the two fragments in the same orientation as in the pNPRsubH1 starting plasmid. The plasmid lacking the internal RsaI fragments was designated pNPRsubH1Δ.

EXAMPLE 11

Replacement of the Neutral Protease Gene with a Deletion Mutant

Plasmid pNPRsubh1Δ was transformed into B. subtilis strain BG2019 (the subtilisin deleted mutant from Example 6) and chromosomal integrants were selected on skim milk plates. Two types of Cm$^r$ transformants were noted, those with parental levels of proteolysis surrounding the colony, and those with almost no zone of proteolysis. Those lacking a zone of proteolysis were picked restreaked to purify individual colonies, and their protease deficient character on skim milk plates confirmed. One of the Cm$^r$, proteolysis deficient colonies was chosen for further studies (designated BG2034). Spontaneous Cm$^s$ revertants of BG2034 were isolated by overnight growth in LB media containing no Cm, plating for individual colonies, and replica plating on media with and without Cm. Three Cm$^s$ revertants were isolated, two of which were protease proficient, one of which was protease deficient (designated BG2036). Hybridization analysis of BG2036 confirmed that the plasmid had been lost from this strain, probably by recombination, leaving only the deletion fragments of subtilisin and neutral protease.

EXAMPLE 12

Phenotype of Strains Lacking Functional Subtilism and Neutral Protease

The growth, sporulation and expression of proteases was examined in strains lacking a functional gene for either the neutral or alkaline protease or both. The expression of proteases was examined by a zone of clearing surrounding a colony on a skim milk plate and by measurement of the protease levels in liquid culture supernatants (Table B). A strain (BG2035) carrying the subtilisin gene deletion, and showed a 30 percent reduction level of protease activity and a normal halo on milk plates. Strain BG2043, carrying the deleted neutral protease gene and active subtilisin gene, and constructed by transforming BG16 (Ex. 8) with DNA from BG2036 (Example 11), showed an 80 percent reduction in protease activity and only a small halo on the milk plate. Strain BG2054, considered equivalent to BG2036

TABLE B

Effect of protease deletions on protease expression and sporulation.

| | Genotype[a] | Protease activity[b] | Percent Sporulation |
|---|---|---|---|
| BG16 | Wild type | 100 | 40 |
| BG2035 | aprΔ684 | 70 | 20 |
| BG2043 | nprEΔ522 | 20 | 20 |
| BG2054 | aprΔ684,nprEΔ522 | ND | 45 |
| BG84(pBS42) | spoOAΔ677,prt-77 | ND | — |
| BG84(pNPR10) | spoOAΔ677,prt-77 | 3000 | — |

[a]Only the loci relevant to the protease phenotype are shown.
[b]Protease activity is espressed in arbitrary units, BG16 was assigned a level of 100. ND indicates the level of protease was not detectable in the assay used.

Strain BG2054, considered equivalent to BG2036 (Example 11) in that it carried the foregoing deletions in both genes, showed no detectable protease activity in this assay and no detectable halo on milk plates. The deletion of either or both of the protease genes had no apparent effect on either growth or sporulation. Strains carrying these deletions had normal growth rates on both minimal glucose and LB media. The strains sporulated at frequencies comparable to the parent strain BG16. Examination of morphology of these strains showed no apparent differences from strains without such deletions.

EXAMPLE 13

Site-specific Saturation Mutagenesis of the B. Amyloliquefaciens Subtilism Gene at Position 222; Preparation of the Gene for Cassette Insertion pS4-5, a derivative of pS4 made according to Wells et al., "Nucleic Acids Res.", 1983, 11:7911-7924 was digested with EcoRI and BamHI, and the 1.5 kb EcoRI-BamHI fragment recovered. This fragment was ligated into replicative form M-13 mp9 which had been digested with EcoRI and BamHI (Sanger et al., 1980, "J. Mol. Biol." 143 161-178. Messing et al, 1981, "Nucleic Acids Research" 9, 304-321. Messing, J. and Vieira, J. (1982) Gene 19, 269-276). The M-13 mp9 phage ligations, designated M-13 mp9 SUBT, were used to transform E. coli strain JM101 and single stranded phage DNA was prepared from a two mL overnight culture. An oligonucleotide primer was synthesized having the sequence 5'-GTACAACGGTACCTCACG-CACGCTGCAGGAGCGGCTGC-3'. This primer conforms to the sequence of the subtilis gene fragment encoding amino acids 216–232 except that the 10 bp of codons for amino acids 222–225 were deleted, and the codons for amino acids 220, 227 and 228 were mutated to introduce a KpnI site 5' to the met-222 codon and a PstI site 3' to the met+222 codon. See FIG. 12. Substituted nucleotides are denoted by asterisks, the underlined codons in line 2 represent the new restriction sites and the scored sequence in line 4 represents the inserted oligonucleotides. The primer (about 15 μM) was labelled with [$^{32}$p] by incubation with [$\gamma^{32}$p]-ATP (10 μL in 20 μL reaction)(knersham 5000 Ci/mmol, 10218) and T$_4$ polynucleotide kinase (10 units) followed by non-radioactive ATP (100 μM) to allow complete phosphorylation of the mutagenesis primer. The kinase was inactivated by heating the phosphorylation mixture at 68° C. for 15 min.

The primer was hybridized to M-13 mp9 SUBT as modified from Norris et al., 1983, "Nucleic Acids Res." 11, 5103–5112 by combining 5 μL of -the labelled mutagenesis primer (~3 μM), ~1 μg M-13 mp9 SUBT template, 1 μL of 1 μM M-13 sequencing primer (17-mer), and 2.5 μL of buffer (0.3M Tris pH 8, 40 mM MgCl 21 12 mM EDTA, 10 mM DTT 0.5e mg/ml BSA). The mixture was heated to 68° C. for 10 minutes and cooled 10 minutes at room temperature. To the annealing mixture was added 3.6 μL of 0.25 mM DGTP, DCTP, DATP, and DTTP, 1.25 μL of 10 mM ATP, 1 μL ligase (4 units) and 1 μL Klenow (5 units). The primer extension and ligation reaction (total volume 25 pl) proceeded 2 hours at 14° C. The Klenow and ligase were inactivated by heating to 68° C. for 20 min. The heated reaction mixture was digested with BamH1 and EcoRI and an aliquot of the digest was applied to a 6 percent polyacrylamide gel and radioactive fragments were visualized by autoradiography. This showed the [$^{32}$p] mutagenesis primer had indeed been incorporated into the EcoRI-BamH1 fragment containing the now mutated subtilisin gene.

The remainder of the digested reaction mixture was diluted to 200 μL with 10 mM Tris pH 8, containing 1 mM EDTA, extracted once with a 1:1 (v:v) phenol/-chloroform mixture, then once with chloroform, and the aqueous phase recovered. 15 μL of 5M ammonium acetate (pH 8) was added along with two volumes of ethanol to precipitate the DNA from the aqueous phase. The DNA was pelleted by centrifugation for five minutes in a microfuge and the supernatant was discarded. 300 μL of 70 percent ethanol was added to wash the DNA pellet, the wash was discarded and the pellet lyophilized.

pBS42 from example 4 above was digested with BamH1 and EcoRI and purified on an acrylamide gel to recover the vector. 0.5 μg of the digested vector, 50 μM ATP and 6 units ligase were dissolved in 20 μl of ligation buffer. The ligation went overnight at 14° C. The DNA was transformed into E. coli 294 rec+ and the transformants grown in 4 ml of LB medium containing 12.5 μg/ml chloramphenicol. Plasmid DNA was prepared from this culture and digested with KpnI, EcoRI and BamHI. Analysis of the restriction fragments showed 30-50 percent of the molecules contained the expected KpnI site programmed by the mutagenesis primer. It was hypothesized that the plasmid population not including the KpnI site resulted from M-13 replication before bacterial repair of the mutagenesis site, thus producing a heterogenous population of KpnI+ and KpnI− plasmids in some of the transformants. In order to obtain a pure culture of the KpnI+plasmid, the DNA was transformed a second time into E. coli to clone plasmids containing the new KpnI site. DNA was prepared from 16 such transformants and six were found to contain the expected KpnI site.

Preparative amounts of DNA were made from one of these six transformants (designated pΔ222) and restriction analysis confirmed the presence and location of the expected KpnI and PstI sites. 40 μg of pΔ222 were digested in 300 μL of KpnI buffer plus 30 μL KpnI (300 units) for 1.5 h at 37° C. The DNA was precipitated with ethanol, washed with 70 percent ethanol, and lyophilized. The DNA pellet was taken up in 200 μL HindIII buffer and digested with 20 μL (500 units) PstI for 1.5 h at 37° C. The aqueous phase was extracted with phenol/CHCl$_3$ and the DNA precipitated with ethanol. The DNA was dissolved in water and purified by polyacrylamide gel electrophoresis. Following electroelution of the vector band (120 v for 2 h at 0° C. in 0.1 times TBE (Maniatis et al., Id.)) the DNA was purified by phenol/CHCl$_3$ extraction, ethanol precipitation and ethanol washing.

Although pΔ222 could be digested to completion (>98 percent) by either KnpI or PstI separately, exhaustive double digestion was incomplete (<<50 percent). This may have resulted from the fact that these sites were so close (10 bp) that digestion by KnpI allowed "breathing" of the DNA in the vicinity of the PstI site, i.e., strand separation or fraying. Since PstI will only cleave double stranded DNA, strand separation could inhibit subsequent PstI digestion.

EXAMPLE 14

Ligation of Oligonucleotide Casettes into the Subtilism Gene

10 μM of four complementary oligonucleotide pools (A-D, Table 1 below) which were not 5' phosphorylated were annealed in 20 μl ligase buffer by heating for five minutes at 68° C. and then cooling for fifteen minutes at room temperature. 1 μM of each annealed oligonucleotide pool, ~0.2 μg KpnI and PstI-digested pΔ222 obtained in Example 13, 0.5 mM ATP, ligase buffer and 6 units T$_4$ DNA ligase in 20 μL total volume was reacted overnight at 14° C. to ligate the pooled cassettes in the vector. A large excess of cassettes (~300×over the pΔ222 ends) was used in the ligation to help prevent intramolecular KpnI-KpnI ligation. The reaction was diluted by adding 25 μL of 10 mM Tris pH 8 containing 1 mM EDTA. The mixture was reannealed to avoid possible cassette concatemer formation by heating to 68° C. for five minutes and cooling for 15 minutes at room temperature. The ligation mixtures from each pool were transformed separately into E. coli 294 rec+ cells. A small aliquot from each transformation mixture was plated to determine the number of independent transformants. The large number of transformants indicated a high probability of multiple mutagenesis. The rest of the transformants (~200-400 transformants) were cultured in 4 m.1 of LB medium plus 12.5 μg chloramphenicol/ml. DNA was prepared from each transformation pool (A-D). This DNA was digested with KpnI, ~0.1 μg was used to retransform E. coli rec+ and the mixture was Plated to isolate individual colonies from each pool. Ligation of the cassettes into the gene and bacterial repair upon transformation destroyed the KpnI and PstI sites. Thus, only pΔ222 was cut when the transformant DNA was digested with KpnI. The cut plasmid would not transform E. coli. Individual transformants were grown in culture and DNA was prepared from 24 to 26 transformants per pool for direct plasmid sequencing. A synthetic oligonucleotide primer having the sequence 5'-GAGCTT-GATGTCATGGC-3' was used to prime the dideoxy sequencing reaction. The mutants which were obtained are described in Table C below.

Two codon+222 mutants (i.e., gln and ile) were not found after the screening described. To obtain these a single 25mer oligonucleotide was synthesized for each mutant corresponding to the top oligonucleotide strand in FIG. 12. Each was phosphorylated and annealed to the bottom strand of its respective nonphosphorylated oligonucleotide pool (i.e., pool A for gln and pool D for ile). This was ligated into KpnI and PstI digested pΔ222 and processed as described for the original oligonucleotide pools. The frequency of appearance for single mutants obtained this way was 2/8 and 0/7 for gln and ile, respectively. To avoid this apparent bias the top strand was phosphorylated and annealed to its unphosphorylated complementary pool. The heterophosphorylated cassette was ligated into cut PΔ222 and processed as before. The frequency of appearance of gln and ile mutants was now 7/7 and 7/7, respectively.

The data in Table C demonstrate a bias in the frequency of mutants obtained from the pools. This probably resulted from unequal representation of oligonucleotides in the pool. This may have been caused by unequal coupling of the particular trimers over the mutagenesis codon in the pool. Such a bias problem could be remedied by appropriate adjustment of trimer levels during synthesis to reflect equal reaction. In any case, mutants which were not isolated in the primary screen were obtained by synthesizing a single strand oligonucleotide representing the desired mutation, phosphorylating both ends, annealing to the pool of non-phosphorylated complementary strands and ligating into the cassette site. A biased heteroduplex repair observed for the completely unphosphorylated cassette may result from the fact that position 222 is closer to the 5' end of the upper strand than it is to the 5' end of the lower strand (see FIG. 12). Because a gap exists at the unphosphorylated 5' ends and the mismatch bubble in the double stranded DNA is at position 222, excision repair of the top strand gap would more readily maintain a circularly hybridized duplex capable of replication. Consistent with this hypothesis is the fact that the top strand could be completely retained by selective 5' phosphorylation. In this case only the bottom strand contained a 5' gap which could promote excision repair. This method is useful in directing biased incorporation of synthetic oligonuclotide strands when employing mutagenic oligonucleotide cassettes.

EXAMPLE 15

Site-Specific Mutagenesis of the Subtilism Gene at Position 166

The procedure of Examples 13–14 was followed in substantial detail, except that the mutagenesis primer differed (the 37 mer shown in FIG. 13 was used), the two restriction enzymes were SacI and XmaIII rather than PstI and KpnI and the resulting constructions differed, as shown in FIG. 13.

Bacillus strains excreting mutant subtilisins at position 166 were obtained as described below in Example 16. The mutant subtilisins exhibiting substitutions of ala, asp, gln, phe, his, lys, asn, arg, and val for the wild-type residue were recovered.

EXAMPLE b 16

Preparation of Mutant Subtilism Enzymes

B. subtilis strain BG2036 obtained by the method of Example 11 was transformed by the plasmids of Examples 14, 15 or 20 and by pS4-5 as a control. Transformants were plated or cultured in shaker flasks for 16 to 48 h at 37° C. in LB media plus 12.5 μg/ml chloramphenicol. Mutant enzymatically active subtilisin was recovered by dialyzing cell broth against 0.01M sodium phosphate buffer, pH 6.2. The dialyzed broth was then titrated to pH 6.2 with 1N HCl and loaded on a 2.5×2 cm column of CM cellulose (CM-52 Whatman). After washing with 0.01M sodium phosphate, pH 6.2, the subtilisins (except mutants at position +222) were eluted with the same buffer made 0.08N in NaCl. The mutant subtilisins at position +222 were each eluted with 0.1M sodium phosphate, pH 7.0. The purified mutant and wild type enzymes were then used in studies of oxidation stability, Km, Kcat, Kcat/Km ratio, pH optimum, and changes in substrate specificity.

TABLE C

| Pool | Oligonucleotide Pool Organization and Frequency of Mutants Obtained | | |
|---|---|---|---|
| | Amino Acids | Codon-222[a] | Frequency[b] |
| A | asp | GAT | 2/25 |
| | met | ATG | 3/25 |
| | cys | TGT | 13/25 |
| | arg | AGA | 2/25 |
| | gln | GAA | 0/25 |
| | unexpected mutants[c] | | 5/25 |
| B | leu | CTT | 1/25 |
| | pro | CCT | 3/25 |
| | phe | TTC | 6/25 |
| | tyr | TAC | 5/25 |
| | his | CAC | 1/25 |
| | unexpected mutants | | 9/25 |
| C | glu | GAA | 3/17 |
| | ala | GCT | 3/17 |
| | thr | ACA | 1/17 |
| | lys | AAA | 1/17 |
| | asn | AAC | 1/17 |
| | unexpected mutants | | 8/17 |
| D | gly | GGC | 1/23 |
| | trp | TGG | 8/23 |
| | ile | ATC | 0/23 |
| | ser | AGC | 1/23 |
| | val | GTT | 4/23 |
| | unexpected mutants | | 9/23 |

[a]Codons were chosen based on frequent use in the cloned subtilisin gene sequence (Wells et al., 1983, Id.).
[b]Frequency was determined from single track analysis by direct plasmid sequencing.
[c]Unexpected mutants generally comprised double mutants with changes in codons next to 222 or at the points of ligation. These were believed to result from impurities in the obigonucleotide pools and/or erroneous repair of the gapped ends.

EXAMPLE 17

Mutant Subtilism Exhibiting Improved Oxidation Stability

Subtilisins having cysteine and alanine substituted at the 222 position for wild-type methionine (Example 16) were assayed for resistance to oxidation by incubating with various concentrations of sodium hypochloride (Clorox Bleach).

To a total volume of 400 μl of 0.1M, pH 7, NaPO4 buffer containing the indicated bleach concentrations (FIG. 14) sufficient enzyme was added to give a final concentration of 0.016 mg/ml of enzyme. The solutions were incubated at 25° C. for 10 min. and assayed for enzyme activity as follows: 120 μl of either ala+222 or wild type, or 100 μl of the cys+222 incubation mixture was combined with 890 μl 0.1M tris buffer at pH 8.6 and 10 μl of a sAAPFpN (Example 18) substrate solution (20 mg/ml in DMSO). The rate of increase in absorbance at 410 nm due to release of p-nitroaniline (Del Mar, E. G., et al., 1979 "Anal. Biochem." 99, 316–320) was monitored. The results are shown in FIG. 14. The alanine substitution produced considerably more stable enzyme than either the wild-type enzyme or a mutant in which a labile cysteine residue was substituted for methionine. Surprisingly, the alanine substitution did not substantially interfere with enzyme activity against the assay substrate, yet conferred relative oxidation stability on the enzyme. The serine+222 mutant also exhibited improved oxidation stability.

EXAMPLE 18

Mutant Subtilisms Exhibiting Modified Kinetics and Substrate Specificity

Various mutants for glycine+166 were screened for modified Kcat, Km and Kcat/Km ratios. Kinetic parameters were obtained by analysis of the progress curves of the reactions. The rate of reaction was measured as a function of substrate concentration. Data was analyzed by fitting to the Michaelis-Menton equation using the non-linear regression algorithm of Marquardt (Marquardt, D. W. 1963, "J. Soc. Ind. Appl. Math." 11, 431–41). All reactions were conducted at 25° C. in 0.1M tris buffer, pH 8.6, containing benzoyl-L-Valyl-Glycyl-L-Arginyl-P-nitroanilide (BVGRpN; Vega Biochemicals) at initial concentrations of 0.0025M to 0.00026M (depending on the value of Km for the enzyme of interest—concentrations were adjusted in each measurement so as to exceed Km) or succinyl-L-Alanyl-L-Alanyl-L-Prolyl-L-Phenylalanyl-p-nitroanilide (sAAPFpN; Vega Biochemicals) at initial concentrations of 0.0010M to 0.00028M (varying as described for BVGRpN).

The results obtained in these experiments were as follows:

TABLE D

| Substrate | Enzyme | Kcat (s$^{-1}$) | Km (M) | Kcat/Km |
|---|---|---|---|---|
| sAAPFpN | gly-166 (wild type) | 37 | $1.4 \times 10^{-4}$ | $3 \times 10^5$ |
| | ala + 166 | 19 | $2.7 \times 10^{-5}$ | $7 \times 10^5$ |
| | asp + 166 | 3 | $5.8 \times 10^{-4}$ | $5 \times 10^3$ |
| | glu + 166 | 11 | $3.4 \times 10^{-4}$ | $3 \times 10^4$ |
| | phe + 166 | 3 | $1.4 \times 10^{-5}$ | $2 \times 10^5$ |
| | hys + 166 | 15 | $1.1 \times 10^{-4}$ | $1 \times 10^5$ |
| | lys + 166 | 15 | $3.4 \times 10^{-5}$ | $4 \times 10^5$ |
| | asn + 166 | 26 | $1.4 \times 10^{-4}$ | $2 \times 10^5$ |
| | arg + 166 | 19 | $6.2 \times 10^{-5}$ | $3 \times 10^5$ |
| | val + 166 | 1 | $1.4 \times 10^{-4}$ | $1 \times 10^4$ |
| BVGRpN | Wild Type | 2 | $1.1 \times 10^{-3}$ | $2 \times 10^3$ |
| | asp + 166 | 2 | $4.1 \times 10^{-5}$ | $5 \times 10^4$ |
| | glu + 166 | 2 | $2.7 \times 10^{-5}$ | $7 \times 10^4$ |
| | asn + 166 | 1 | $1.2 \times 10^{-4}$ | $8 \times 10^3$ |

The Kcat/Km ratio for each of the mutants varied from that of the wild-type enzyme. As a measure of catalytic efficiency, these ratios demonstrate that enzymes having much higher activity against a given substrate can be readily designed and selected by screening in accordance with the invention herein. For example, A166 exhibits over 2 times the activity of the wild type on sAAPFpN.

This data also demonstrates changes in substrate specificity upon mutation of the wild type enzyme. For example, the Kcat/Km ratio for the D166 and E166 mutants is higher than the wild type enzyme with the BVGPN substrate, but qualitatively opposite results were obtained upon incubation with sAAPFpN. Accordingly, the D166 and E166 mutants were relatively more specific for BVGRpN than for sAAPFpN.

EXAMPLE 19

Mutant Subtilism Exhibiting Modified PH-Activity Profile

Figure 15:
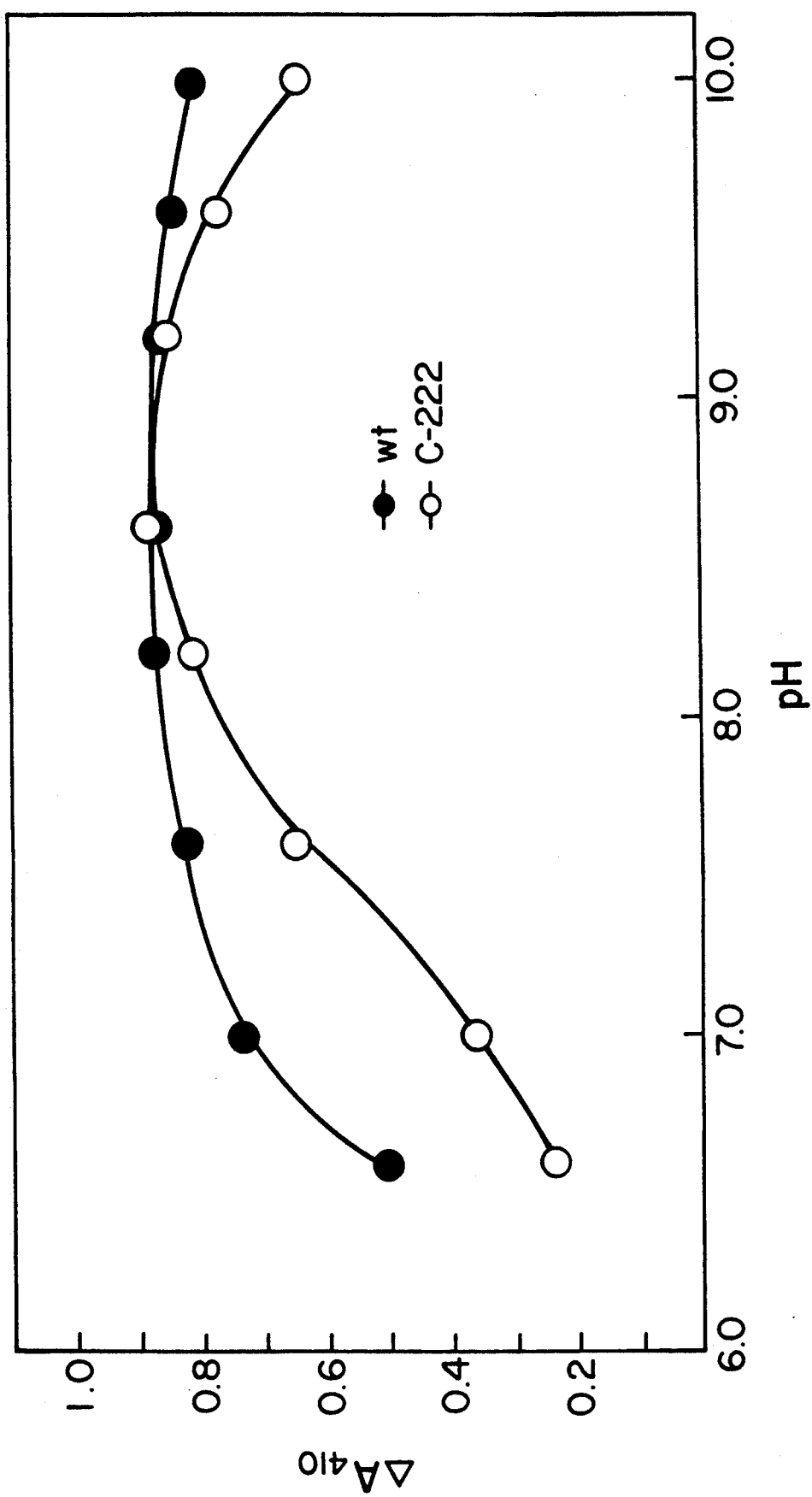
FIG. 15 demonstrates a change in the ph-activity profile of a subtilisin mutant when compared to the wild type enzyme.

The pH profile of the Cys+222 mutant obtained in Example 16 was compared to that of the wild type enzyme. 10 μl of 60 mg/ml sAAPFpN in DMSO, 10 μl of Cys+222 (0.18 mg/ml) or wild type (0.5 mg/ml) and 980 μl of buffer (for measurements at pH 6.6, 7.0 and 7.6, 0.1M NAPO4 buffer; at pH 8.2, 8.6 and 9.2, 0.1M tris buffer; and at pH 9.6 and 10.0, 0.1M glycine buffer), after which the initial rate of change in absorbance at 410 nm per minute was measured at each pH and the data plotted in FIG. 15. The Cys+222 mutant exhibits a sharper pH optimum than the wild type enzyme.

EXAMPLE 20

Site-Specific Mutagenesis of the Subtilisin Gene at Position 169

The procedure of Examples 13–14 was followed in substantial detail, except that the mutagenesis primer differed (the primer shown in FIG. 16 was used), the two restriction enzymes were KpnI and EcoRV rather than PstI and KpnI and the resulting constructions differed, as shown in FIG. 16.

Bacillus strains excreting mutant subtilisins at position 169 were obtained as described below in Example 16. The mutant subtilisins exhibiting substitutions of ala and ser for the wild-type residue were recovered and assayed for changes in kinetic features. The assay employed SAAPFPN at pH 8.6 in the same fashion as set forth in Example 18. The results were as follows:

TABLE E

| Enzyme | Kcat (s$^{-1}$) | Km (M) | Kcat/Km |
|---|---|---|---|
| ala + 169 | 58 | $7.5 \times 10^{-5}$ | $8 \times 10^5$ |
| ser + 169 | 38 | $8.5 \times 10^{-5}$ | $4 \times 10^5$ |

EXAMPLE 21

Alterations in Specific Activity on a Protein Substrate

Position 166 mutants from Examples 15 and 16 were assayed for alteration of specific activity on a naturally occuring protein substrate. Because these mutant proteases could display altered specificity as well as altered specific activity, the substrate should contain sufficient different cleavage sites i.e., acidic, basic, neutral, and hydrophobic, so as not to bias the assay toward a protease with one type of specificity. The substrate should also contain no derivitized residues that result in the masking of certain cleavage sites. The widely used substrates such as hemoglobin, azocollogen, azocasein, dimethyl casein, etc., were rejected on this basis. Bovine casein, α and α2 chains, was chosen as a suitable substrate.

A 1 percent casein (w/v) solution was prepared in a 100 mM Tris buffer, pH 8.0, 10 mM EDTA. The assay protocol is as follows:

790 μl 50 mM Tris pH 8.2
100 μl I percent casein (Sigma) solution
10 μl test enzyme (10-200 μg).

This assay mixture was mixed and allowed to incubate at room temperature for 20 minutes. The reaction was terminated upon the addition of 100 μl 100 percent trichloroacetic acid, followed by incubation for 15 minutes at room temperature. The precipitated protein was pelleted by centrifugation and the optical density of the supernatant was determined spectrophotometrically at 280 nm. The optical density is a reflection of the amount of unprecipitated, i.e., hydrolyzed, casein in the reaction mixture. The amount of casein hydrolysed by each mutant protease was compared to a series of standards containing various amounts of the wild type protease, and the activity is expressed as a percentage of the corresponding wild type activity. Enzyme activities were converted to specific activity by dividing the casein hydrolysis activity by the 280 nm absorbance of the enzyme solution used in the assay.

All of the mutants which were assayed showed less specific activity on casein than the wild type with the exception of Asn+166 which was 26 percent more active on casein than the wild type. The mutant showing the least specific activity was ile+166 at 0.184 of the wild type activity.

What is claimed is:

1. An isolated, normally sporulating mutant Bacillus which produces no detectable proteolytic activity in a skim milk plate or casein assay during any phase of its growth, wherein said lack of detectable proteolytic activity is due to chromosomal deletions of one or more naturally occurring codons specifying the mature subtilisin protease and a mature neutral protease.

2. A Bacillus according to claim 1 wherein the deletion of the naturally occurring codons of the mature subtilisin protease and the mature neutral protease coding genes, is within the coding region of such mature subtilisin protease and mature neutral protease coding genes.

3. A method for producing a normally sporulating mutant Bacillus incapable of producing enzymatically active subtilisin and neutral protease during any phase of its growth, wherein said method comprises:
   a. constructing the following plasmids in any order:
      (1) a plasmid which comprises:
         i) a selectable marker; and
         ii) a deletion of the mature *Bacillus subtilisin* gene;
      wherein the plasmid is capable of integration into the Bacillus chromosomal DNA at the region of homology between the chromosomal subtilisin gene and the in vitro created deletion;
      (2) a plasmid which comprises:
         i) a selectable marker; and
         ii) a deletion of the mature Bacillus neutral protease gene;
      wherein the plasmid is capable of integration into the Bacillus chromosomal DNA at the region of homology between the chromosomal neutral protease gene and the in vitro created deletion;
   b) transforming a plurality of Bacillus organisms capable of producing subtilisin with the plasmid of step a) (1);
   c) selecting transformants comprising the selectable marker present in the plasmid of step a) (1);
   d) selecting those transformants from those selected in step c) wherein the subtilisin is inactive or deficient;
   e) existing the plasmid from the chromosome of the transformants in step d); and
   f) repeating steps b) through e) above with the plasmid of step a) (2), provided that the deletions can be made in any order and provided that steps b) through e) can be performed with either plasmid in any order.

4. A method according to claim 3 wherein the Bacillus is a *Bacillus subtilis*.

* * * * *